(12) United States Patent
Van Gelder et al.

(10) Patent No.: US 8,214,041 B2
(45) Date of Patent: Jul. 3, 2012

(54) OPTIMIZATION OF AV INTERVALS IN SINGLE VENTRICLE FUSION PACING THROUGH ELECTROGRAM MORPHOLOGY

(75) Inventors: Berry M. Van Gelder, Nuenen (NL); M. S. J. Pilmeyer, Sittaro (NL); John E Burnes, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 133 days.

(21) Appl. No.: 11/109,432

(22) Filed: Apr. 19, 2005

(65) Prior Publication Data
US 2006/0235478 A1    Oct. 19, 2006

(51) Int. Cl.
*A61N 1/365* (2006.01)
*A61N 1/362* (2006.01)
*A61N 1/36* (2006.01)

(52) U.S. Cl. .................... 607/25; 607/9; 607/4
(58) Field of Classification Search ............... 607/2, 4, 607/9, 11, 15, 25–28; 600/510
See application file for complete search history.

(56) References Cited

U.S. PATENT DOCUMENTS

| | | | | |
|---|---|---|---|---|
| 4,303,075 A | * | 12/1981 | Heilman et al. | 607/4 |
| 5,514,163 A | * | 5/1996 | Markowitz et al. | 607/9 |
| 5,527,347 A | * | 6/1996 | Shelton et al. | 607/9 |
| 5,534,016 A | * | 7/1996 | Boute | 607/9 |
| 5,626,620 A | * | 5/1997 | Kieval et al. | 607/9 |
| 5,713,930 A | * | 2/1998 | van der Veen et al. | 607/25 |
| 5,716,383 A | * | 2/1998 | Kieval et al. | 607/9 |
| 5,749,906 A | * | 5/1998 | Kieval et al. | 607/9 |
| 6,832,112 B1 | * | 12/2004 | Bornzin | 607/9 |
| 7,020,522 B1 | * | 3/2006 | Hoijer et al. | 607/27 |
| 2002/0095183 A1 | * | 7/2002 | Casset et al. | 607/4 |
| 2003/0083700 A1 | * | 5/2003 | Hill | 607/9 |
| 2004/0158293 A1 | * | 8/2004 | Yonce et al. | 607/9 |
| 2004/0172078 A1 | | 9/2004 | Chinchoy | |
| 2004/0181260 A1 | | 9/2004 | Anderson et al. | |
| 2004/0215252 A1 | | 10/2004 | Verbeek et al. | |
| 2005/0209648 A1 | * | 9/2005 | Burnes et al. | 607/9 |
| 2005/0209650 A1 | * | 9/2005 | Van Gelder et al. | 607/25 |

FOREIGN PATENT DOCUMENTS

EP    1529551 A1    11/2005

* cited by examiner

*Primary Examiner* — Carl H. Layno
*Assistant Examiner* — Jon-Eric C. Morales
(74) *Attorney, Agent, or Firm* — Reed A. Duthler; Stephen W. Bauer

(57) ABSTRACT

This document provides a simple and automatic method for determining an optimal AV interval and/or range of AV intervals for, in an exemplary embodiment, LV-only pacing. Such a method provides significant advantages for patients while reducing burdens related to post-implant follow-up by clinicians in that it greatly reduces the need for doing echocardiographic-based AV interval optimization procedures as well as providing a way to dynamically optimize AV intervals as the patient moves about their activities of daily living (ADL).

23 Claims, 14 Drawing Sheets

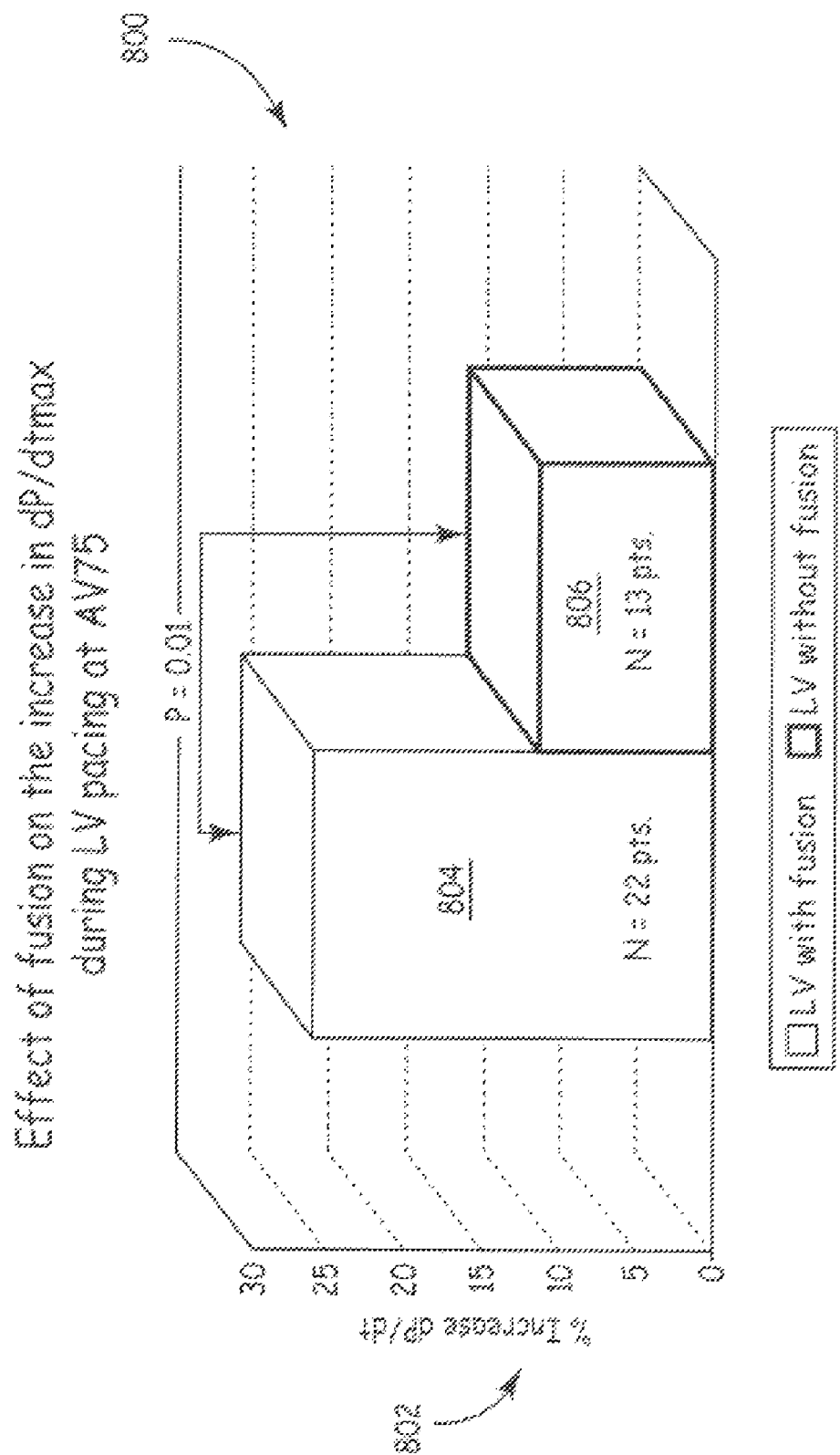

OPTIMIZATION OF AV INTERVALS IN SINGLE VENTRICLE FUSION PACING THROUGH ELECTROGRAM MORPHOLOGY

CROSS REFERENCE TO RELATED APPLICATIONS

This patent document relates to co-pending non-provisional U.S. patent application by Burnes and Mullen entitled, "APPARATUS AND METHODS OF ATRIAL-BASED BI-VENTRICULAR FUSION PACING" and bearing U.S. patent application Ser. No. 10/803,570 and co-pending non-provisional U.S. patent application by Pilmeyer and van Gelder entitled, "APPARATUS AND METHODS FOR 'LEPARS' INTERVAL-BASED FUSION PACING" having U.S. patent application Ser. No. 10/802,419 each of which was filed on 17 Mar. 2004 and the entire contents thereof is hereby fully incorporated by reference herein.

FIELD OF THE INVENTION

The present invention thus provides a simple and automatic method for determining an optimal AV interval and/or range of AV intervals for LV-only pacing. Such a method provides significant advantages for patients while reducing burdens related to post-implant follow-up by clinicians in that it greatly reduces the need for doing echocardiographic-based AV interval optimization procedures as well as providing a way to dynamically optimize AV intervals as the patient moves about their activities of daily living (ADL).

BACKGROUND OF THE INVENTION

Cardiac resynchronization therapy (CRT) is a promising and accepted device therapy for patients with systolic heart failure classified in New York Heart Association (NYHA) class III and IV. Current (2003) indications include patients who, despite optimal medication, are symptomatic, and who demonstrate LV asynchrony. The latter occurs in patients with left bundle branch block (LBBB) and typically presents with a QRS width (measured on an ECG machine) of greater than about 130-150 milliseconds (ms). Herein, "asynchrony" is characterized by a delay in systolic contraction between the intraventricular septum and the left ventricular (LV) free wall.

Currently available CRT bi-ventricular pacing generally employs one lead positioned in operative communication with the right ventricle (RV) and one lead in operative communication with a portion of one of the tributaries of the coronary venous system. The myocardial venous system provides a pathway for deployment of LV stimulation of the lead (and associated electrodes) to operatively communicate with the LV. In most patients, an additional lead is deployed to the right atrium (RA) for atrioventricular (AV) synchronization during pacing. Exceptions for placement of the atrial lead include patients suffering from chronic atrial fibrillation (AF) or having a relatively high AF "burden." According to such CRT delivery, electrical stimulation of both the RV and LV operates to assist ventricular asynchrony and increase contractility (as measured by ventricular pressure development (dP/dt)). For certain patients, further assistance of contractility can be achieved by variation of the inter-ventricular ("V-V") interval. The V-V interval is the interval of time between LV and RV stimulation (or vice versa), which is a programmable parameter in currently available pulse generators (implantable, temporary and/or external). Optimization of the V-V interval can be performed on the guidance of echocardiographic or hemodynamic parameters as is known in the art.

In several studies it has been observed that LV pacing is hemodynamically superior or at least equal to bi-ventricular pacing. However, the inventors suggest that to date little or no attention has been paid to the mechanism(s) behind the observation.

In a U.S. patent to Hill, U.S. Pat. No. 6,871,096 entitled, "System and Method for Bi-Ventricular Fusion Pacing," which issued on 22 Mar. 2005 Hill purports to have discovered that in certain patients exhibiting symptoms resulting from congestive heart failure (CHF), cardiac output is enhanced by timing the delivery of an LV pacing pulse such that evoked depolarization of the LV is triggered by a sensed intrinsic depolarization of the RV. The conclusion was based on the notion that a "fusion" depolarization enhances cardiac output in cardiac patients where the RV depolarizes first due to intact A-V conduction of a preceding intrinsic or evoked atrial depolarization wave front, but the A-V conducted depolarization of the LV is unduly delayed. The fusion depolarization of the LV is attained by timing the delivery of an LV-PACE pulse to follow, in time, the intrinsic depolarization of the RV but to precede, in time, the intrinsic depolarization of the LV. Accordingly, an RV-PACE pulse is not delivered due to the inhibition of the RV-PACE upon the occurrence of a sensed RV-EVENT, allowing natural propagation of the wave front and depolarization of the septum, while an LV-PACE pulse is prematurely delivered in fusion with the RV depolarization. The entire contents of the '096 patent is hereby incorporated by reference herein.

However, due to a number of factors (e.g., the amount of time required for appropriate signal processing, confounding conduction delays or conduction blockage of a patient, electrode placement and the like) for a variety of patients A CRT delivery system that takes all these factors into consideration is needed.

Specifically, there is a need for structures, methods and processes to efficiently and chronically deliver and control of pacing therapy to effect ventricular fusion in cardiac patients who might otherwise not receive similar benefits from bi-ventricular CRT therapy.

SUMMARY

The present invention relates to a novel means of determining the appropriate AV interval timing for LV-only pacing therapy delivery based on an evaluation of inter-ventricular conduction time (IVCT) between the RV and the LV. The inventors have empirically shown that LV hemodynamic response to appropriately timed LV-only ventricular pacing stimulation rivals LV hemodynamic response to bi-ventricular pacing (including CRT) for a majority of patients. The inventors believe that ventricular fusion is achieved when a depolarization wavefront evoked by LV-only pacing merges with an intrinsic depolarization wavefront (propagated via the right bundle branch). According to the invention, fusion between this pair of depolarization wavefronts (one intrinsically activated, one activated via pacing stimulus) is achieved by controlling the IVCT by adjustment of the AV interval (e.g., for A-LV pacing) by applying an algorithm that applies a plurality of different AV intervals to produce a range of ventricular activity signals. At one end of this range are intrinsically-dominated signals (e.g., endocardial electrogram or EGM signals) at the other end of the range are pacing-dominated signals (e.g., LV-paced EGM signals).

Within the range of signals the inventors define a transition area or, perhaps less exactly, a transition point having characteristics deemed to represent a fusion/transition therapy signal. Thus, based upon the morphology or certain characteristics of the signals—which can be inspected manually, semi-manually or automatically according to the invention—and a fusion/transition AV interval corresponding to the fusion/transition signal is programmed.

In one form of the invention, fusion/transition AV intervals are programmed for various discrete heart rates or ranges of heart rate. For example, the inventive AV optimization routine can be performed when a patient is sleeping, resting, mildly exercising or undergoing significant physical exertion and to the extent that the fusion/transition AV intervals differ a discrete interval can be programmed that corresponds to the actual heart rate of the patient.

In another form of the invention, two or more sensors can be compared to confirm that uni-ventricular pacing is achieving the desired level or degree of fusion. In a related embodiment, to the extent that a patient experiences any discomfort or becomes symptomatic in response to a programmed fusion/transition AV interval, the AV interval can be altered to reduce the magnitude or frequency of fusion pacing. For example, fusion pacing therapy according to the invention can be applied for a short time, on specific or alternate beats or the like.

A single site can be employed to gather the signals or multiple sites, including sites located remotely from the activated tissue (e.g., subcutaneous or submuscular cardiac sensing locations). As noted, the signals can comprise EGM signals but other types of signals can also be utilized to successfully practice the invention. For instance, a peak-to-peak amplitude characteristic; a QT interval characteristic; a temporal location of a positive peak of the signal; a temporal location of a peak derivative of the signal; a temporal location of a negative peak of the signal; a temporal location of a minimum derivative of the signal; at least a portion of a QRS depolarization signal; at least a part of a depolarization-repolarization QRS-T signal; an integral of at least a portion of a QRS depolarization signal; an integral of at least a part of a depolarization-re-polarization QRS-T signal; a wavelet coefficient; a fast Fourier transform coefficient, etc.

The optimum value for what the inventors' refer to as the "LEPARS interval" (derived from: LEft ventricular PAcing, Right ventricular Sensing) can be determined acutely at the time an implantable pulse generator (IPG) is implanted. Thereafter, the operative AV interval can be automatically adjusted pursuant to the algorithm herein described, depicted and claimed to keep the LEPARS interval constant.

In one form of the present invention, a data set optionally configured as a look-up-table (LUT) correlates a plurality of data; for example, LEPARS intervals, heart rates, activity sensor signal inputs, discrete physiologic cardiac timing intervals and the like. Dynamically referencing the data set (e.g., LUT) set an appropriate operating AV delay interval. If a mathematical derivation of heart rate is used to set the LEPARS interval, the data set or a lookup table can comprise at least two data sets or LUTs, one for stable or relatively stable HR, and another for various rate-of-change of the HR to more accurately reflect a physiologic LEPARS interval. Alternatively, the LEPARS pacing modality according to the invention may be terminated in the event of relatively high or unstable heart rates. In fact, the inventors suggest that the LEPARS pacing modality cease and/or a pacing mode switch is performed to a non-atrial tracking mode in the event that an arrhythmia is detected (esp. atrial fibrillation or "AF"). More generally, multiple LUTs may be utilized that correlate to one or more physiologic parameters (e.g., containing AV intervals for both paced and intrinsic atrial activation). That is, the data set should provide operating AV intervals that maintain the LEPARS interval (i.e., the elapsed time between an LVp event and the resulting RVs event) over a broad range of heart rates.

Among other aspects, the present invention provides an energy-efficient manner of providing fusion-pacing therapy providing immediate improved contractility and maximum (LV) pressure development. A pacing stimulus is provided to the LV as is known in the art (e.g., via an electrode deployed into a portion of the coronary sinus, great vein, and branches thereof or epicardially) and the time interval (LEPARS interval) between LV pacing delivery and sensed depolarization of the RV is maintained. As depicted herein, an atrial pacing/sensing lead operatively couples to an atrial chamber, a pacing lead operatively couples to the LV, and a sensing lead couples to the RV.

A variety of locations for the atrial lead can be used to successfully practice the methods of the present invention. For example, electrical communication (e.g., pacing and sensing an atrial chamber) with the RA can utilize a uni-polar or bi-polar electrode arrangement in either an epicardial or endocardial location. Similarly, depolarizations of the ventricles can utilize any known sensing vector (e.g., tip-to-ring, coil-to-can, coil-to-coil, etc.). An endocardial location may include the common RA pacing site of the RA appendage although RA septal or other locations are acceptable. An electrode operatively coupled to the LA may also be used, including such locations as the CS and portions distal to the os of the CS, as well as the inter-atrial septal wall, among others.

In addition, one or more mechanical, acoustic and/or activity sensors may be coupled to the heart and used to confirm that a desired amount of ventricular synchrony results from the fusion pacing therapy. Some representative mechanical sensors for this purpose include fluid pressure sensors or acceleration sensors and the like. The mechanical sensors operatively couple to the heart (e.g., LV lateral free-wall, RV septal wall, epicardial RV locations, etc.). Output signals from such sensors may be used to modify the timing of the fusion-pacing stimulus, especially during episodes such as a rapidly changing heart rate.

In addition to the therapy delivery aspects of the present invention, a discrete few therapy delivery guidance or security options may be used to determine if the fusion pacing therapy ought to be modified, initiated or discontinued. For example, in the event a transient conduction anomaly interrupting AV conduction is detected a pacing modality switch to a double or triple chamber pacing modality could be implemented (e.g., DDD). In the event that the LEPARS interval decreases or increases relative to a prior calibrated or operating value a similar pacing mode switch can be implemented, fusion-pacing could cease or the AV interval adjusted. If one of the sensors indicates increasing ventricular asynchrony or decreasing hemodynamic response to the therapy, the fusion pacing therapy can be modified or cease. Furthermore, from time-to-time the fusion pacing therapy could be suspended while cardiac activity is monitored so that any change in normal sinus rhythm, or improvement in ventricular synchrony or performance (e.g., desirable so-called "reverse remodeling") can be accommodated. In the event that ventricular synchrony and conduction improves markedly, or that the suspension of fusion-based CRT results in improved hemodynamics, a pacing mode switch from fusion-based CRT to a very energy efficient physiologic, single stimulus, atrial-based pacing mode such as AAI, ADI, AAI/R, ADI/R and the like may be implemented. Thereafter, in the event that conduction anomalies cause ventricular asynchrony and resultant hemodynamic compromise or a heart failure decompensation event, another pacing mode switch can be implemented to resume an fusion-pacing mode according to the present invention.

As mentioned, pacing the LV alone can result in cardiac resynchronization provided that an appropriate AV interval is utilized thus resulting in a single fusion-type ventricular contraction initiated by both intrinsic-RV conduction and paced-LV conduction. Fusion and LEPARS pacing are methods that have been previously disclosed to achieve CRT through LV-only pacing, but they have not provided detailed methods for automatically optimizing the AV interval at which the LV should be paced. These methods have relied on determining the intrinsic A-RV sense time as an estimate of when the RV activation has occurred, with one suggested embodiment including a technique wherein the LV should be paced 20-30 milliseconds (ms) prior to the expiration of an intrinsic A-RV interval to achieve optimal single ventricular paced, fusion-type CRT. The inventors of the present invention discovered that LV-only ventricular pacing alters the typical waveform morphology of the RV EGM and concluded that these alterations reflect changes in the direction of the activation (or depolarization) wavefront approaching the sense electrodes on the RV lead. With short AV intervals, the activation wavefront arrives at the RV lead from a paced-LV wavefront (on an LV-pace dominant EGM). With longer AV intervals, the activation wavefront arrives at the RV lead from the intrinsic RV depolarization (Intrinsic RV dominant EGM). At intermediate AV intervals, there is a fusion of the LV and RV depolarization wavefronts over the RV electrode, producing a distinct EGM morphology. At AV intervals greater than this transition point provide pressure development in the LV (LV dP/dt$_{max}$) of greater magnitude than at AV intervals less than or equal to the transition point. This invention thus utilizes these phenomena to provide a method to automatically identify the optimal AV interval for LV-only fusion-pacing based on EGM morphology changes. Inventive apparatuses and methods of optimizing AV intervals can be operated manually, periodically, aperiodically, continuously and/or upon command or patient trigger.

The present invention thus provides a simple and automatic method for determining an optimal AV interval and/or range of AV intervals for LV-only pacing. Such a method provides significant advantages for patients while reducing burdens related to post-implant follow-up by clinicians in that it greatly reduces the need for doing echocardiographic-based AV interval optimization procedures as well as providing a way to dynamically optimize AV intervals as the patient moves about their activities of daily living (ADL).

Additionally, methods are described for detecting changes in EGM morphology associated with shifts from RV sensing to LV pacing or visa versa.

The foregoing and other aspects and features of the present invention will be more readily understood from the following detailed description of the embodiments thereof, when considered in conjunction with the drawings, in which like reference numerals indicate similar structures throughout the several views.

BRIEF DESCRIPTION OF THE DRAWINGS

FIG. 8 graphically depicts a comparison of percentage increase in pressure development ("% increase dP/dt") for LV-only pacing therapy delivery at AV$_{75}$ to 35 patients (the 22 developed fusion and the 13 that did not).

DETAILED DESCRIPTION OF THE ILLUSTRATED EMBODIMENTS

Figure 1:
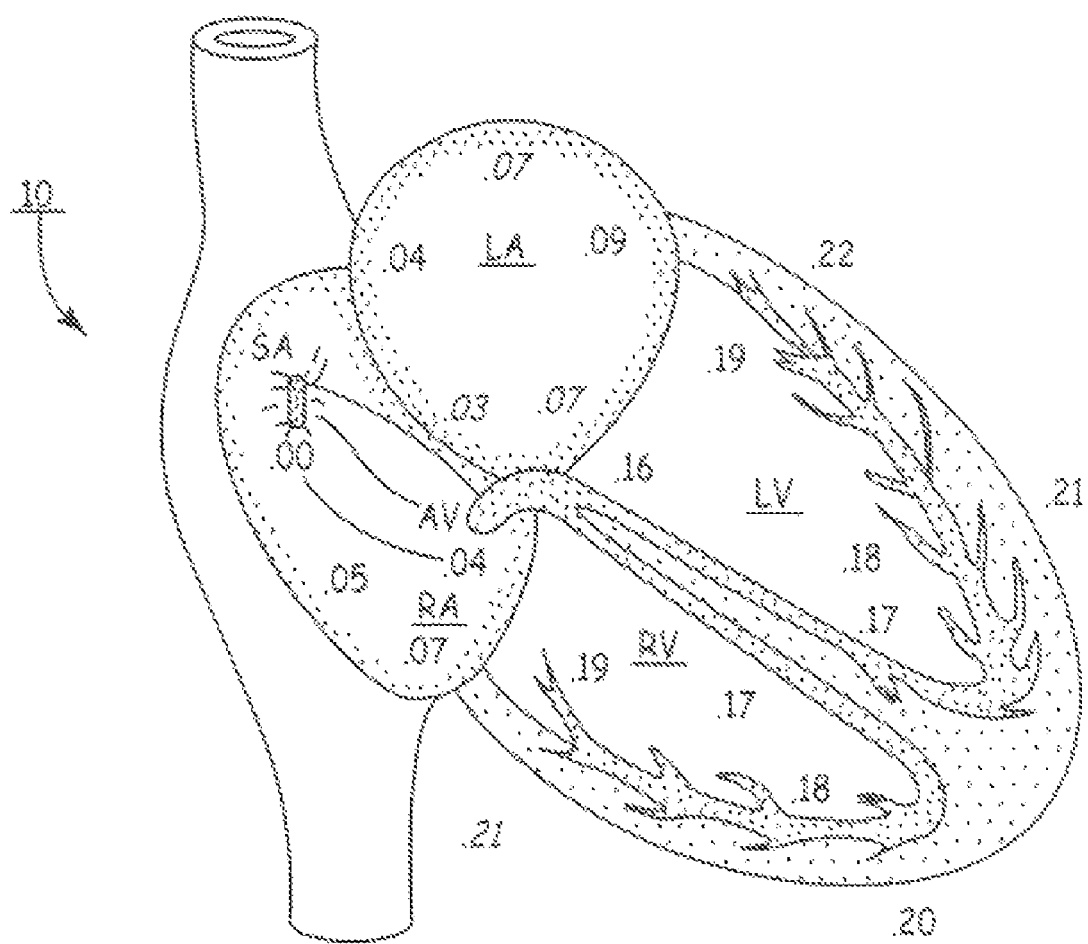
FIG. 1 is an illustration of transmission of the cardiac depolarization waves through the heart in a normal intrinsic electrical activation sequence.

In a prior study for the optimization of AV and V-V intervals, development of pressure in the LV (e.g., dP/dt) for a triple-chamber IPG was utilized as a hemodynamic parameter reflecting LV contractility. In one protocol, a measurement of dP/dt during RV-only pacing was studied (as function of the AV interval). Observation at the time yielded a conclusion that a 100 ms AV interval (ARV$_{00}$) is the longest AV interval at which no (electrocardiographic-based as opposed to mechanically-based) ventricular fusion occurred during RV-only pacing. Subsequently the effect of an AV interval of 75%, 50% and 25% of the longest value was measured (in the drawings appended hereto referred to as AV$_{75}$, AV$_{50}$, and ALV25$_5$ respectively). After these measurements were made the protocol was continued with LV-only pacing employing the same AV intervals. Surprisingly, fusion was not observed during RV-only pacing, whereas fusion was observed during LV pacing (at ARV$_{00}$ and in 60% of the patients at AV$_{75}$). The QRS tracings depicting the presence of fusion is presented in FIG. 6 (wherein an ECG lead (RV) shows QRS morphology during delivery of RV-only and LV-only pacing therapy). During RV pacing no fusion was observed and during LV-only pacing fusion was observed to be present for AV intervals of 120 ms to 180 ms (see EGM traces 672,674,676 of FIG. 6).

Figure 9A:
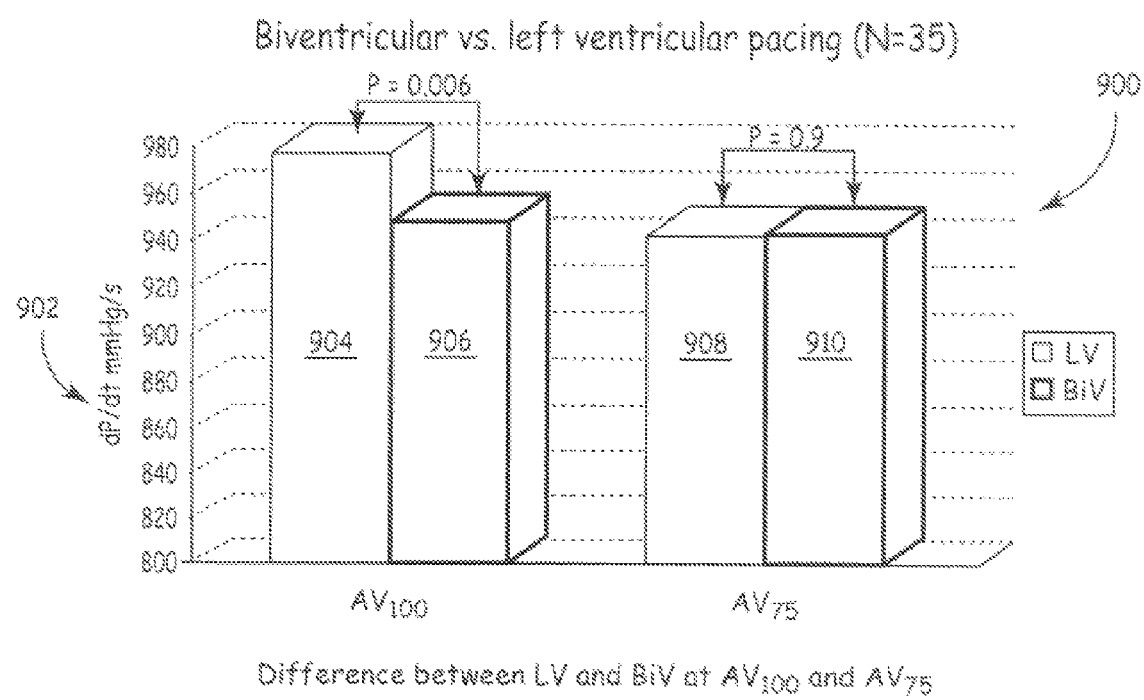
FIGS. 9A and 9B graphically depicts comparison of pressure development (dP/dt) for LV-only pacing and bi-ventricular pacing at two different AV intervals (AV$_{100}$ and AV$_{75}$).
Figure 9B:
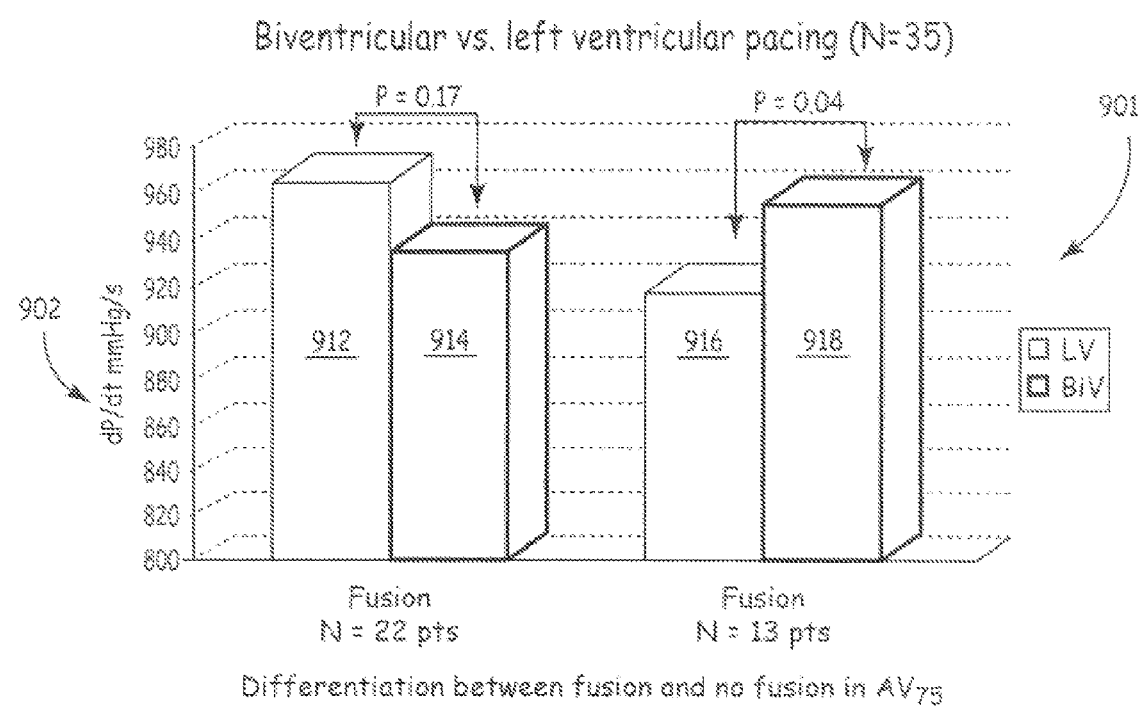

FIG. 9A depicts a comparison 900 of developing pressure (dP/dt) with bi-ventricular pacing versus LV-only ventricular pacing at two AV intervals ($ARV_{00}$ and $AV_{75}$). Inspection of FIG. 9A illustrates superior hemodynamic effects of the inventive fusion therapy according to the present invention (e.g., higher $dP/dt_{max}$ for LV pacing—of about 979 mmHg/s—than for bi-ventricular pacing—of about 949 mmHg/s) which is highly statistically significant (p=0.006). Assuming that fusion is achieved and maintained for a range of operating AV intervals, the hemodynamics of LV fusion according to the invention are believed to be superior to bi-ventricular pacing therapy. With reference to FIG. 8,9 (wherein an AV interval that produced fusion in response to LV-only pacing in all patients is referred to as $AV_{100}$) an AV interval of 75% of the maximum (denoted $AV_{75}$) produced LV-only fusion depolarization for just over 60% of the patients during LV-only pacing. That is, the percentage of patients with fusion at $AV_{75}$ is illustrated in FIG. 8 (22/35=63%). Referring again to FIG. 9A, the comparison illustrates that at $AV_{75}$, LV pacing shows a trend towards a higher pressure rate-of-change (dP/dt) than bi-ventricular pacing (i.e., $dP/dt_{max}$ for LV pacing was 902 mmHg/s while for biventricular pacing the value was 888 mmHg/s). Turning now to FIG. 9B illustrates at 901 maximum pressure development ($dP/dt_{max}$) at $AV_{75}$ for patients that achieved LV-only pacing fusion and those that did not achieve fusion. Inspection of FIG. 9B reveals the following: of the 22 patients that achieved LV-only pacing fusion showed a trend towards a higher $dP/dt_{max}$ (as depicted at 912) than they did when receiving bi-ventricular pacing (as depicted at 914) of 964 mmHg/s versus 938 mmHg/s. In contrast, patients who did not achieve LV-only pacing fusion fared poorly when compared to pressure development from bi-ventricular pacing (919 mmHg/s vs. 957 mmHg/s) as depicted at 916,918. The inventors thus posit that LV-only pacing according to the invention that produces fusion of pacing-induced and intrinsically-activated ventricular depolarization wavefronts results in developed ventricular pressure ($dP/dt_{max}$) of equal or greater magnitude than bi-ventricular pacing. Left ventricular pacing and fusion within this context means LV stimulation associated with intrinsic conduction via the right bundle branch. Left ventricular pacing with fusion can be recognized from a surface ECG (or intra-cardiac electrogram or "EGM"). This implies that the degree of fusion is determined by the interval between LV pacing and RV sensing (the LEft ventricular PAcing, Right ventricular Sensing interval, or "LEPARS interval"). Accordingly, the inventors assert that the degree of fusion between LV pacing and intrinsic right bundle branch activation is determined by the LEPARS interval (i.e., the elapsed time from LV stimulation to a sensed, intrinsic right bundle branch activation of the RV). According to the invention, an optimum value of the LEPARS interval, somewhat analogous to the V-V interval of traditional bi-ventricular pacing, is implemented chronically to provide a hemodynamic advantage over RV-only pacing and bi-ventricular pacing. In addition, LV-only pacing according to the invention also requires less valuable energy compared to bi-ventricular pacing therapy.

In addition, the inventors also found that the LEPARS interval should be maintained by controlling the operating AV interval for an IPG during pacing therapy delivery. That is, assuming a static LEPARS interval the operating AV interval determines whether fusion will be present and the magnitude of the fusion. Assuming that the LV is stimulated before intrinsic activation of the LV occurs (via the right bundle branch due to the LBBB defective conduction condition), three (3) scenarios arise, as depicted in FIG. 5A-D. In FIG. 5A and FIG. 5B, an atrial pace ("AP") event is followed by a LV pace ("VP") event at an AV interval of 350 ms and 300 ms, respectively. The RV EGMs for these pacing sequences appears fairly closely aligned with the R-wave of the evoked depolarization and thus, the RV depolarization resulted from intrinsic conduction via the right bundle and no fusion was achieved. In FIG. 5C, the atrial pacing stimulus was followed by LV pacing delivery at 250 ms and LV fusion was observed. In FIG. 5D, an AV interval or 200 ms was employed and delayed activation was observed from the left ventricular stimulus (without fusion).

Stated another way, the three scenarios include:

1.) LV fusion can be achieved from LV pacing stimulation and RV intrinsic activation via the right bundle. In this scenario, the LEPARS interval is shorter than the inter-ventricular conduction time (IVCT). As noted above, the IVCT consists of the interval between LV pacing delivery and the later arrival of the LV depolarization wavefront at the electrode disposed in operative electrical communication with the RV. Symbolically, this fusion-generating relationship can be expressed: LEPARS interval<IVCT.

2.) RV fusion can be achieved due to both intrinsic right bundle activation and RV activation caused by a depolarization wavefront from LV pacing therapy delivery. Symbolically, this relationship can be expressed: LEPARS interval=IVCT.

3. No fusion achieved due to activation at the RV sensing electrode(s) from depolarization wavefronts propagated solely from LV pacing stimulus. In this condition, shortening of the AV interval will not affect the LEPARS interval. Symbolically, this relationship can be expressed as: LEPARS interval=IVCT.

Figure 4:
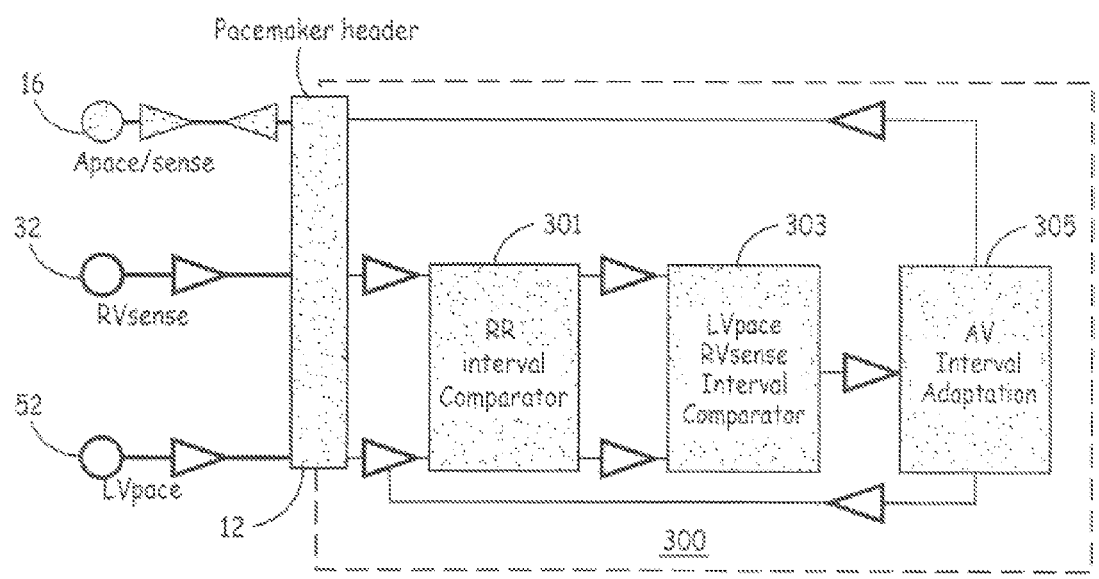
FIG. 4 is schematic representation of the basic principles of a LEPARS interval-driven pacing modality according to the present invention.

From the foregoing, for LV-only pacing a hemodynamic optimum value exists for the LEPARS interval that depends upon timing of a pair of depolarization wavefronts (one evoked in the LV, one intrinsically propagated from the atria). Furthermore, hemodynamic parameters (e.g., $dP/dt_{max}$) and/or echocardiographic parameters (e.g., aortic VTI, TDI) for minimal LV asynchrony can determine this optimum and the concomitant optimized LEPARS interval. Once an optimal LEPARS interval has been determined, it should be operably programmed in the pacing circuitry. The pacemaker should be able to monitor the LEPARS interval and if the interval varies, a feedback system should correct this by adaptation of the AV interval. FIG. 4 represents the schematic illustration of this principle.

By keeping the LEPARS interval at a constant value by adjusting the value of an operating AV delay interval, a pacing system automatically adapts to the appropriate AV interval at higher atrial rates (paced or sensed). This implies that even during exercise, when the intrinsic AV shortens, the LEPARS interval is maintained at its optimum value by adaptation of the AV interval.

Before the LEPARS interval is measured the P-P interval should be compared to a mean value of a previous number of cardiac cycles (e.g., 4-, 8-, 16-, 32-cycles). This comparison should avoid ventricular pacing with an inappropriate AV interval on premature atrial beats or other arrhythmias causing a sudden variation in intrinsic AV conduction. In the event such events occur, the pacing system should revert to bi-ventricular pacing with a relative short AV interval in order to maintain resynchronization therapy.

The inventors suggest that the LEPARS interval-based pacing therapy should be applied only in patients with normal intrinsic AV conduction (and LBBB conduction status). It should not be used as a "stand alone" system, but should be a programmable option in bi-ventricular systems for selected patients. Furthermore, the LEPARS interval-based pacing therapy should not be used in patients with irregular heart rhythms, like atrial fibrillation (AF). For example, if AF is detected in a patient with LV pacing using the LEPARS interval-based pacing modality, a mode switch should occur to a non-tracking mode with bi-ventricular pacing.

In the following detailed description, references are made to illustrative embodiments for carrying out an energy efficient, LEPARS interval-based pacing modality according to the present invention. It is understood that other embodiments may be utilized without departing from the scope of the invention. For example, the invention is disclosed in detail herein in the context of an intrinsically-based or AV sequential (evoked) uni-ventricular single-chamber pacing system operating in an atrial tracking, demand and/or triggered pacing modes. The present invention provides an efficient pacing modality for restoring electromechanical ventricular synchrony based upon either atrial-paced or atrial-sensed events particularly for patients having some degree of either chronic, acute or paroxysmal ventricular conduction block (e.g., intraventricular and/or LBBB). Cardiac pacing apparatus according to the invention are programmable to optionally operate as a dual- or triple-chamber pacing system having an AV synchronous operating mode for restoring upper and lower heart chamber synchronization and right and left atrial and/or ventricular chamber depolarization synchrony. A system according to the invention efficiently provides cardiac resynchronization therapy (CRT) with a single ventricular stimulus per cardiac cycle. In one embodiment, the inventive pacing system operates in a VDD or VDD/R operating mode wherein intrinsic atrial events govern the timing of the AV interval (i.e., herein the A-LVp interval).

The present invention provides enhanced hemodynamic performance for patients having intact nodal conduction but that nevertheless suffer from various forms of heart failure, LV asynchrony, LV dysfunction, and/or ventricular conduction abnormalities. Pacing systems according to the invention can also include rate responsive features and anti-tachyarrhythmia pacing and the like. In addition, a system according to the invention may include cardioversion and/or defibrillation therapy delivery.

In accordance with an aspect of the present invention, a method and apparatus is provided to restore the normal depolarization-repolarization cardiac cycle sequence of FIG. 1 and the synchrony between the RV, septum, and LV that contributes to adequate cardiac output related to the synchronized electromechanical performance of the RV and LV. The foregoing and other aspects of the invention are realized through delivery of cardiac pacing stimulation to a more slowly depolarizing LV that are timed to occur prior to a sensed depolarization in the RV. As a result of such timing, the LV essentially is "pre-excited" so that the electromechanical performance of RV and LV merge into a "fusion event." The amount of temporal pre-excitation provided depends on a number of factors. For example, physiologic conduction delay from the A-V node through the His-Purkinje fibers, electrical conduction delay for sensing intracardiac events (from electrodes through threshold sensing circuitry of a medical device), electrical conduction delay for pacing therapy delivery circuitry, ischemic episodes temporarily tempering conduction pathways, myocardial infarction(s) zones, all can deleteriously impact cardiac conduction. Because the conduction status of a patient can vary over time and/or vary based on other factors such as heart rate, autonomic tone and metabolic status, the present invention provides a dynamically controllable pre-excitation pacing modality. For example, based one or more of several factors, an pre-excitation optimization routine (or sub-routine) can be triggered so that a desired amount of single-chamber fusion-based pacing ensues. Some of the factors include, (i) completion of a pre-set number of cardiac cycles, (ii) pre-set time limit, (iii) loss of capture of the paced ventricle (LV), and/or (iv) physiologic response triggers (e.g., systemic or intracardiac pressure fluctuation, heart rate excursion, metabolic demand increase, decrease in heart wall acceleration, intracardiac electrogram morphology or timing, etc.). The present invention inherently compensates for the particular implantation sites of the pace/sense electrode pair operatively coupled to the LV chamber.

Figure 2:
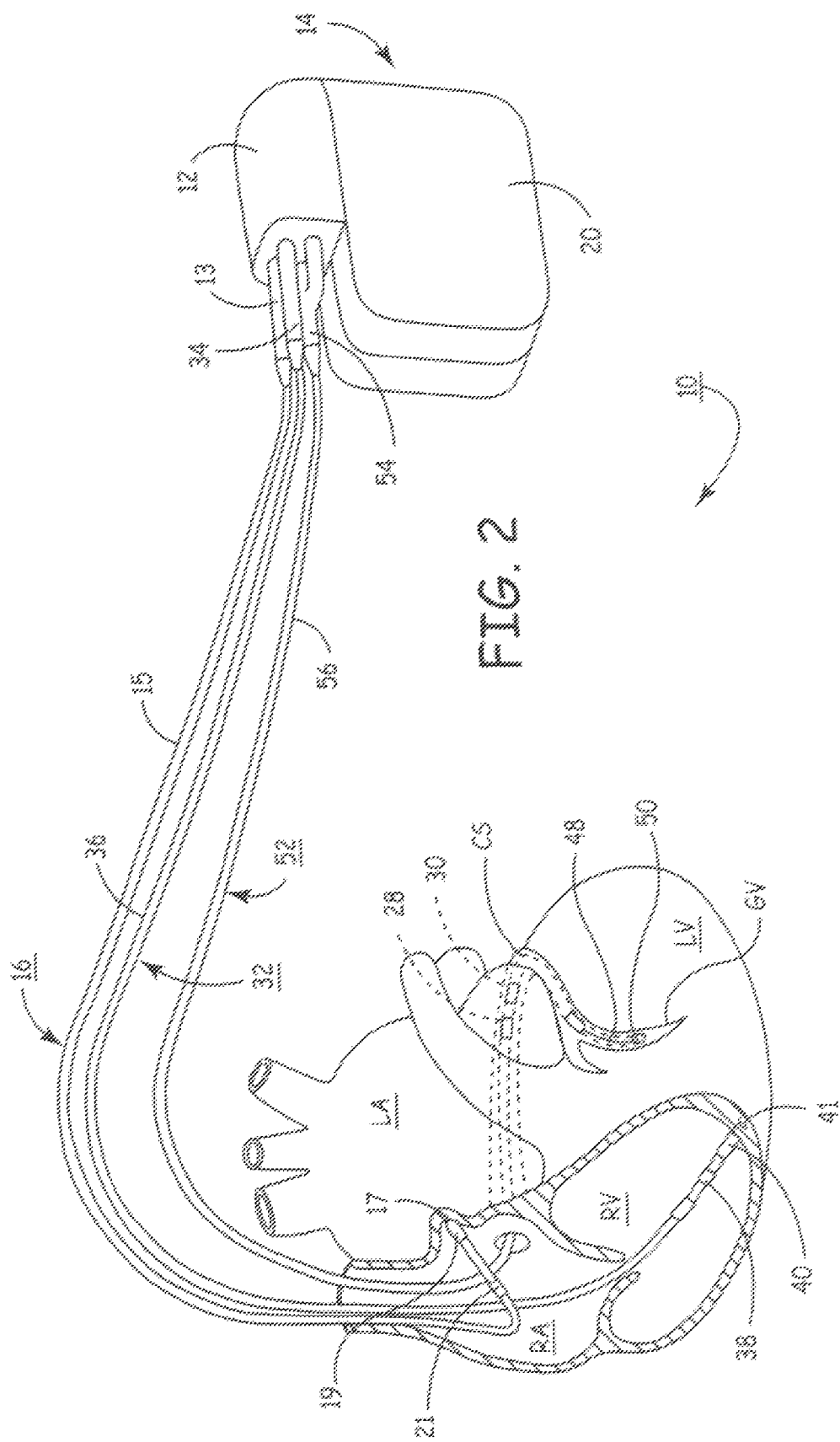
FIG. 2 is a schematic diagram depicting a three channel, atrial and bi-ventricular, pacing system for implementing the present invention.

FIG. 2 is a schematic representation of an implanted, triple-chamber cardiac pacemaker comprising a pacemaker IPG 14 and associated leads 16, 32 and 52 in which the present invention may be practiced. The pacemaker IPG 14 is implanted subcutaneously in a patient's body between the skin and the ribs. The three endocardial leads 16,32,52 operatively couple the IPG 14 with the RA, the RV and the LV, respectively. Each lead includes at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. In addition, mechanical and/or metabolic sensors can be deployed independent of, or in tandem with, one or more of the depicted leads.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this embodiment, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
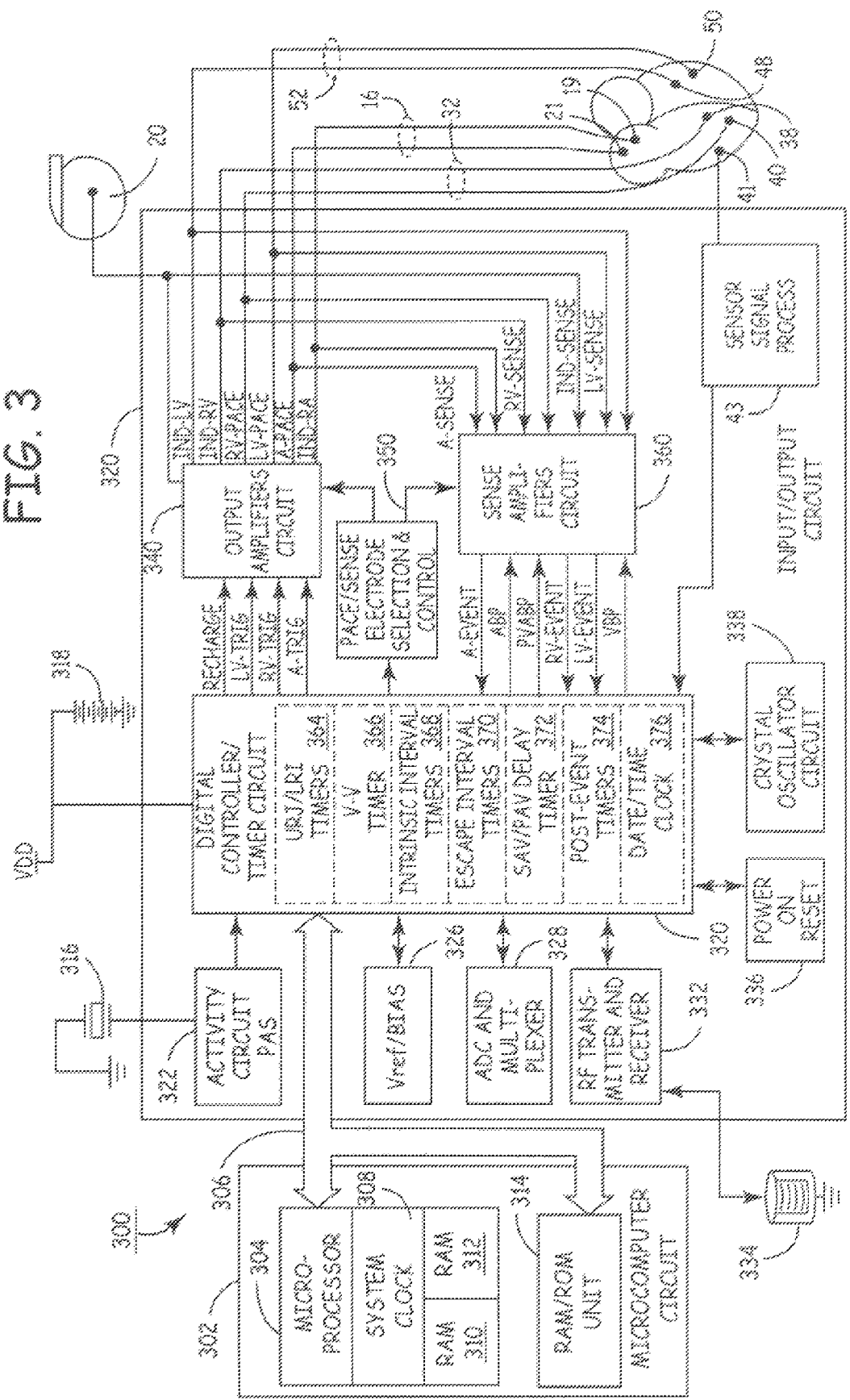
FIG. 3 is a simplified block diagram of one embodiment of IPG circuitry and associated leads employed in the system of FIG. 2 for providing three sensing channels and corresponding pacing channels that selectively functions in an energy efficient ventricular-fusion pacing mode according to the present invention.

Further, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. In addition, at least one physiologic sensor 41 is depicted operatively coupled to a portion of myocardium and electrically coupled to a sensor signal processing circuit 43. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 304 may also serve to define variable AV delays and the uni-ventricular, pre-excitation pacing delay intervals (A-LVp) from the activity sensor data, metabolic sensor(s) and/or mechanical sensor(s).

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay (or A-RVp delay) from a preceding A-EVENT or A-TRIG, a post-ventricular timer 374 for timing post-ventricular time periods, and a date/time clock 376.

Figure 5:
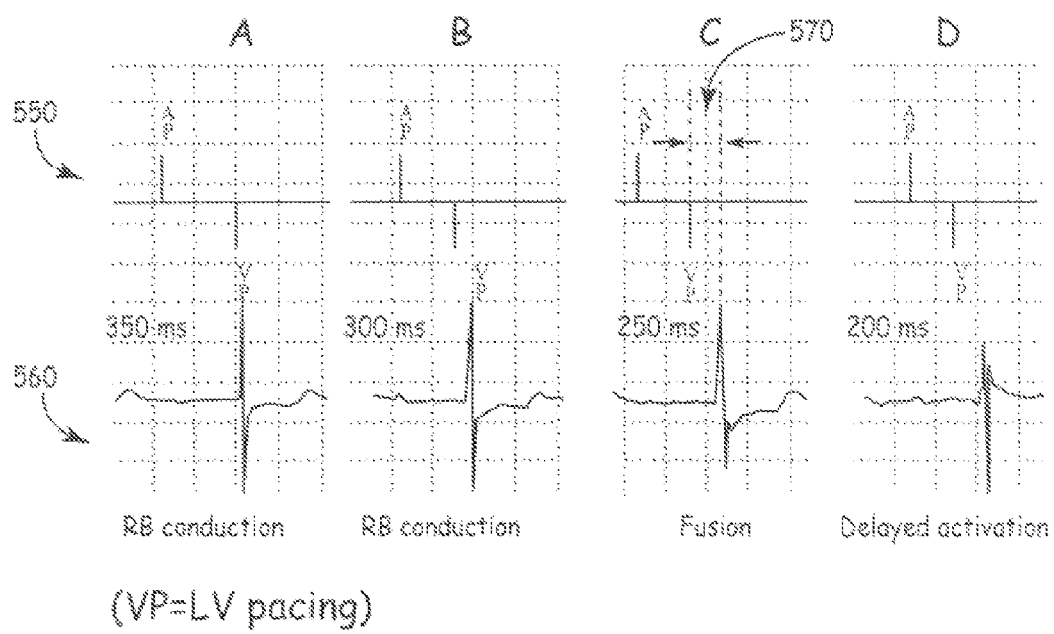
FIG. 5 illustrates four cardiac cycles during which different AV intervals were applied, said AV intervals composed of atrial pacing (AP) and LV pacing (VP) events and the resulting EGM waveforms of the evoked responses.

In the present invention, the AV delay interval timer 372 is loaded with an appropriate PEI delay interval for the LV chamber (i.e., either an A-RVp delay or an A-LVp delay as determined by the flow chart depicted at FIG. 4 and FIG. 5) to time-out starting from a preceding A-PACE or A-EVENT. The interval timer 372 times the PEI, and is based on one or more prior cardiac cycles (or from a data set empirically derived for a given patient) and does not depend on sensing of a depolarization in the other ventricle (i.e., RV) during pre-excitation fusion-based pacing therapy delivery according to the present invention.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Figure 6:
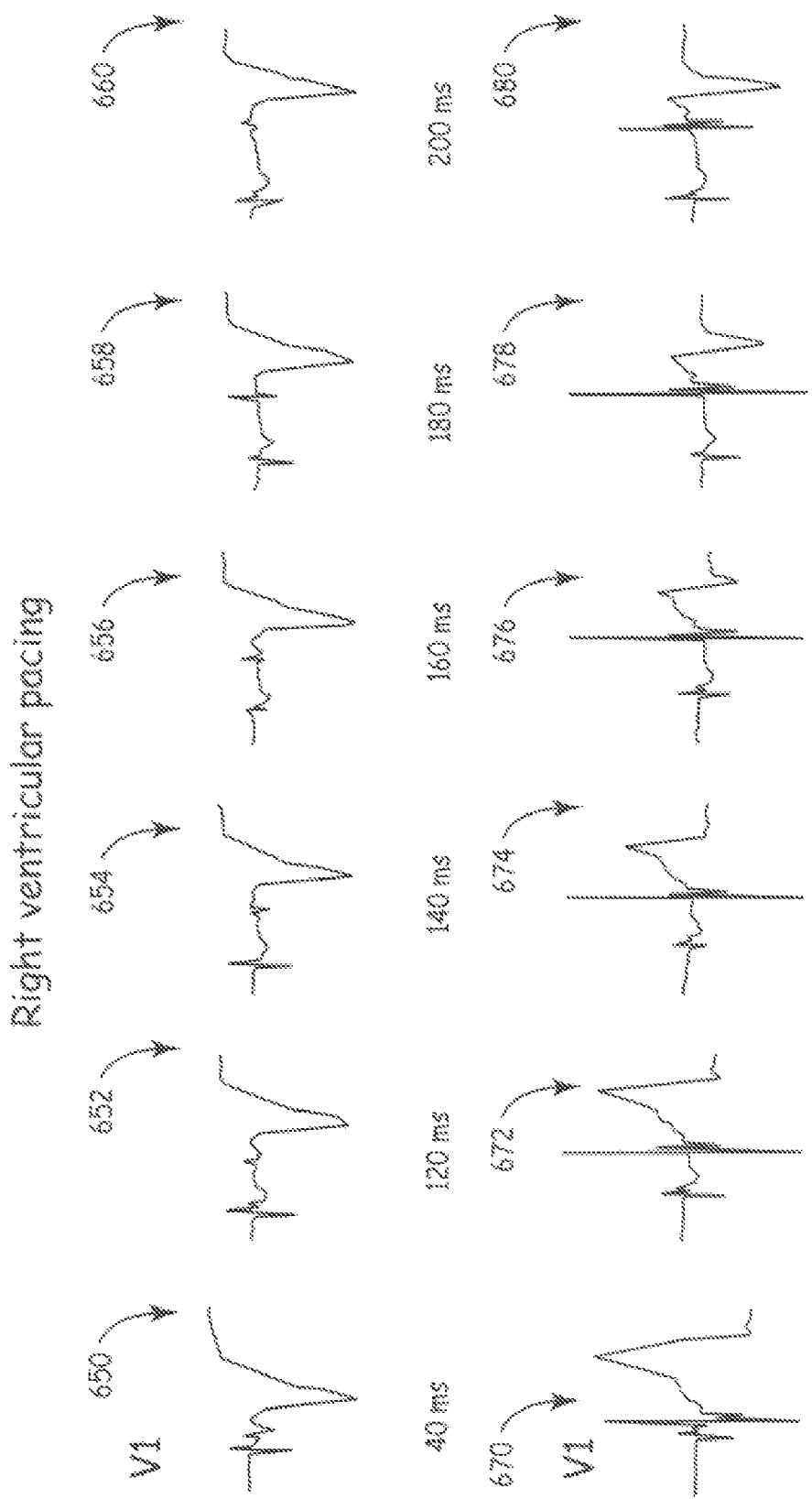
FIG. 6 depicts RV and LV QRS complex morphology during RV and LV pacing at AV intervals ranging from 40 ms to 200 ms.

To simplify the description of FIGS. 4 through 6, it will be assumed that the following references to an "A-EVENT" and "A-PACE" will be the RA-EVENT and RA-PACE, respectively, if there is no LA pacing or sensing provided or programmed on, or will be a programmed one of the RA-EVENT or LA-EVENT and RA-PACE or LA-PACE, respectively.

Turning now to FIG. 4, which schematically represents basic principles of a LEPARS interval-driven pacing modality according to the present invention, the operative circuitry 300 of FIG. 3 includes RR interval comparator 301, coupled to RV sensing electrodes coupled to lead 32, LV pacing electrodes coupled to LV pacing electrodes coupled to lead 52. In turn, the RR interval comparator 301 also couples to LV pace (LVp) and RV sense (RVs) interval comparator 303. An output signal from the LVp and RVs interval comparator 303 serves as an input to AV interval adaptation circuit 305. One of a pair of output signals from the AV interval adaptation circuit 305 operatively connect to atrial sensing and pacing electrodes that are coupled to atrial lead 16. The other of the pair of output signals from the AV interval adaptation circuit 305 operatively connects to LVp electrodes coupled to pacing electrodes coupled to the lead 52.

In operation, the RR interval comparator 301 receives cardiac signals from the heart 10 used to calculate, monitor, measure and/or store information related to various intrinsic and evoked cardiac events (e.g., RV and LV activation sequences and/or R-R intervals via near-field sensing and P-R via near- and far-field sensing and P-P via near-field sensing). The LVp and RVs interval comparator 303 receives information relating to LEPARS interval (i.e., LV pacing-to-RV-sensing) for one or more cardiac cycles and forwards an output signal related thereto to the AV interval adaptation circuit 305. The AV interval adaptation circuit 305 uses at least the measured LEPARS interval and one or more of the cardiac event information to derive an operating AV interval (i.e., A-LVp interval) with an essentially constant LEPARS interval. During an acute procedure, e.g. guided by echo, the optimal LEPARS interval should be determined (e.g., by maximal aortic TDI), this optimal LEPARS interval should be stored into the memory of the pulse generator (e.g. by programming) and the pulse generator should keep this interval essentially constant by varying the A-LVp interval. That is, the pacing electrodes of lead 16 activate the atria and the pacing electrodes of lead 52 activate the LV upon expiration of the A-LVp interval.

FIG. 5A-D illustrates four cardiac cycles (A-D) during which pacing occurred using AV intervals ranging from 350-200 ms, respectively. The AV intervals are composed of the time period between atrial pacing events (labeled "AP") and LV pacing events (labeled "VP') with the resulting RV EGM waveforms of the evoked responses displayed below the depicted intervals. In FIG. 5A, a relatively "late-arriving" (i.e., 350 ms delayed) VP stimulus aligns closely with the sensed evoked depolarization in the RV. The depolarization resulted from the intact conduction pathways (AV node, right Bundle of His and right Purkinje system) which are denoted as "RB" in FIG. 5. In FIG. 5B, the VP stimulus arrives at the LV 300 ms after the AP event (atrial pacing stimulus) and also conducts via the RB without causing any fusion depolarization. In FIG. 5C, the VP stimulus arrives at the LV 250 ms after the delivery of the atrial pacing stimulus, AP, and causes a fusion depolarization. As appreciated by those of skill in the art, the interval between the delivered LV pacing stimulus, VP, and the sensed depolarization (in the RV) constitutes the LEPARS interval. In FIG. 5C, the LEPARS interval is indicated by arrow 570.

FIG. 6 depicts RV and LV QRS complex morphology during RV and LV pacing at AV intervals ranging from 40 ms to 200 ms, at 650-660 and 670-680, respectively. As previously described hereinabove, fusion was not observed during RV pacing at 40, 120, 140, 160, 180 or 200 ms (denoted by reference numerals 650-660) while fusion was observed during LV pacing at 120, 140, 160 and 180 ms (denoted by reference numerals 672, 674, 676, 678).

Figure 7:
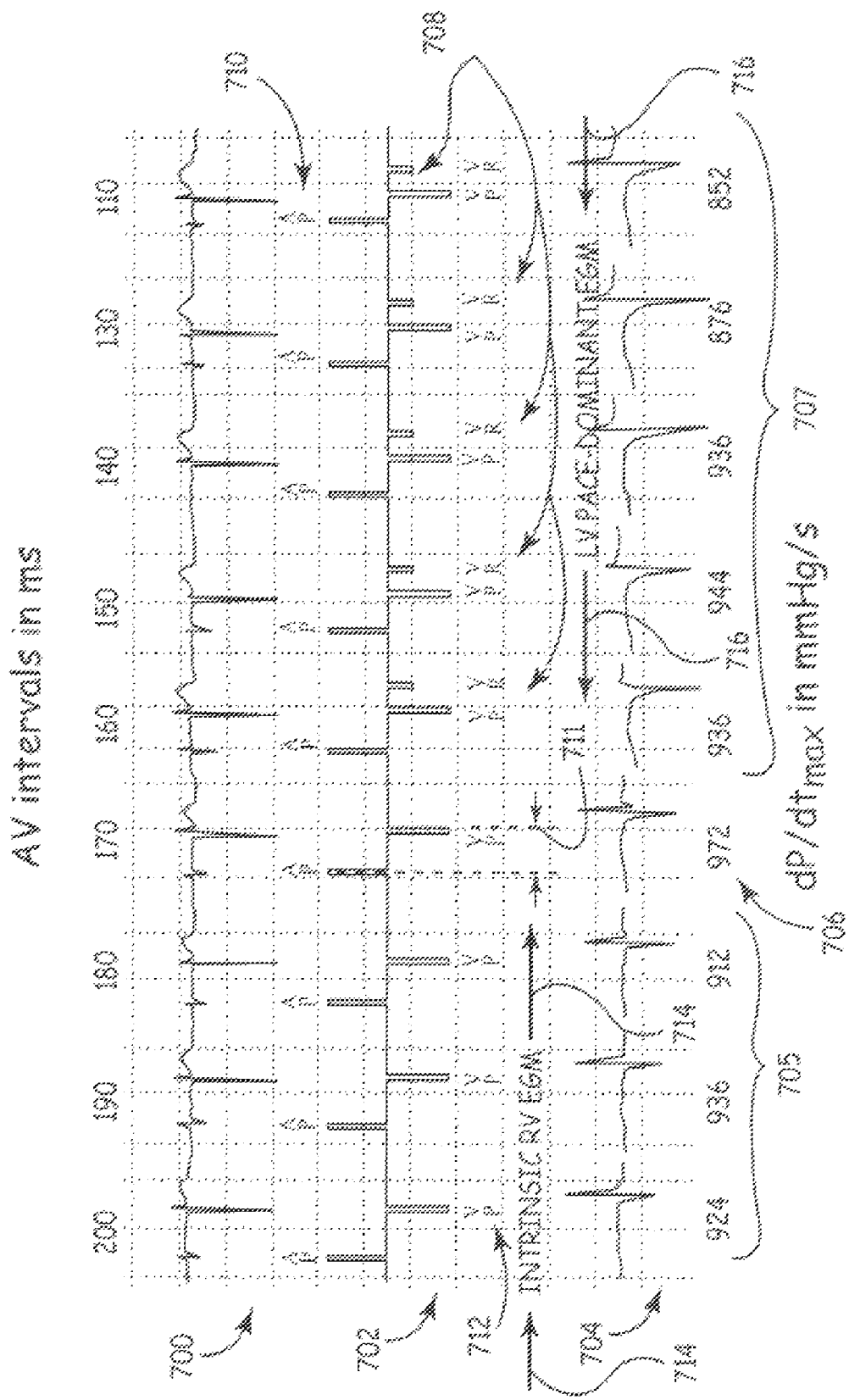
FIG. 7 is a temporal tracing of a surface ECG, a pacing "marker channel" composed of atriai pacing events (AP), LV pacing events (VP), and RV sensing events (VR)—because such events are deemed non-physiologic "refractory" events occurring too soon after the VP events, and resulting LV pressure development (dP/dt$_{max}$).

FIG. 7 is a temporal tracing of a surface ECG (denoted by arrow 700), a pacing "marker channel" composed of atrial pacing events (AP), LV pacing events (VP), and select RV sensing events (VR)—because such events are deemed non-physiologic "refractory" events occurring too soon after the VP events—(denoted by arrow 702), RV EGM (denoted by arrow 704), and resulting LV pressure development expressed as $dP/dt_{max}$ (denoted by arrows 705, 706, 707). The left-hand set of information corresponds to an A-LVp interval of 200 ms with 10 ms decrements for each other set of information (until the right-hand set of information corresponds to 110 ms A-LVp interval). At the relatively shorter AV intervals (denoted by parentheses 707) the LV pacing stimulus is denoted by "VP" and the RV sensed events are denoted as "VR" (708), or ventricular events incorrectly deemed non-physiologic due to the temporal proximity to the VP events. In FIG. 7 (at 707), developed pressure increases as the AV intervals are lengthened from 110 ms to 160 ms although no fusion depolarization have occurred. In contrast, at event 706 with the A-LVp interval set to 170 ms the "marker channel" (at 702) indicates a single VP event (and not independently-sensed "VR" event) and developed pressure reached a relative maximum value (972 mmHg/s). In addition, the morphology of the RV EGM 704 corresponding to the 170 ms AV interval confirms the presence of fusion depolarization(s). Thus, according to the invention, a LEPARS interval 711 promoting fusion resulting from LV-only pacing is defined as the time elapsed from Atrial activation (AP) to sensed RV depolarization (in FIG. 7 concealed as the "VP" event).

FIG. 8 is a graphical depiction 800 comparing percentage increase in pressure development ("% increase dP/dt") 802 for LV-only pacing therapy delivery at $AV_{75}$ to 35 patients. Of the 35 patients, 22 developed fusion (804) and 13 that did not develop fusion (806). FIG. 8 thus appears to confirm the importance of achieving and maintaining ventricular fusion during LV-only pacing therapy delivery. FIG. 8 also provides support for the notion that, for at least some percentage of patients, the operating AV interval (A-LVp interval) may vary over a range of values while still evoking ventricular fusion. One related aspect of the present invention provides slightly greater control freedom during LV-only fusion pacing for those patients that are able to maintain fusion over a wider range of AV intervals. For example, such patients can arguably tolerate continued LV-only fusion pacing over a greater range of AV intervals. For the purposes of the present invention such patients shall be referred to as "fusion responders" who can continue to receive LV-only fusion pacing therapy over a wider range of heart rates before performing a mode switch to a different pacing modality.

FIG. 9A is a graphical depiction comparing pressure development (dP/dt) for LV-only pacing and bi-ventricular pacing at two different AV intervals ($AV_{100}$ and $AV_{75}$). In particular, FIG. 9A depicts a comparison of developing pressure (dP/dt) with bi-ventricular pacing versus LV-only ventricular pacing at the two AV intervals. Inspection of FIG. 9A illustrates that when fusion is achieved during LV-only pacing therapy at 904, greater magnitude of maximum pressure development occurs (dP/dtmax)—of about 979 mmHg/s—than for bi-ventricular pacing 906—of about 949 mmHg/s—which is highly significant (p=0.006). As previously noted, herein a convention has been employed that at $AV_{100}$, all patients developed fusion during LV-only pacing. As illustrated in FIG. 8 and FIG. 9B, at an AV interval of 75% of the maximum ($AV_{75}$), just over 60% of the patients developed fusion depolarizations during LV-only pacing therapy delivery. That is, as shown by FIGS. 8 and 9B, the inventors observed and compared maximum pressure development ($dP/dt_{max}$) at $AV_{75}$ for patients that achieved fusion 804 and those that did not achieve fusion 806. Thus, as shown in FIG. 9B, a higher magnitude pressure development ($dP/dt_{max}$ 902) was observed for the 22 patients during LV-only fusion pacing than during bi-ventricular pacing (as depicted at 904,906 and 912,914), respectively.

Quantitatively, as shown in FIG. 9A wherein pressure development 902 (without distinguishing between patients that developed fusion and those that did not), it was observed that 979 mmHg/s was developed during LV-only fusion pacing according to the invention (at 904) versus about 949 mmHg/s for bi-ventricular pacing (at 906). Note that all patients were paced at $AV_{100}$ in obtaining the data presented at FIG. 9A. In contrast, at $AV_{75}$ measured pressure development between the patients receiving bi-ventricular pacing (at 910) was about the same as those receiving LV-only pacing (at 908). However, as shown in FIG. 9B, when the 13 patients who did not achieve LV pacing-based fusion (916,918)—at least when considered from a hemodynamic perspective—all fared relatively poorly during LV-only pacing (no fusion) than during bi-ventricular pacing (919 mmHg/s versus 957 mmHg/s). Thus, achieving and maintaining fusion is paramount to generating superior hemodynamic effects when delivering LV-only pacing therapy.

The foregoing pressure measurements were obtained using an invasive LV pressure transducer. However, of course a chronically implanted venous pressure transducer (e.g., implanted in the RV) such as the Chronicle® implantable hemodynamic monitor (IHM) can be employed for chronic measurement of developing ventricular pressures. In this form of the invention, a Chronicle IHM and an cardiac IPG can communicate pressure and/or EGM timing information via wireless telemetry so that the IPG can chronically deliver mechanical sensor-confirmed fusion pacing therapy. Of course, the pressure measuring circuitry from the IHM can be included within the housing for an IPG so that a single medical device is utilized to delivery LEPARS interval-based fusion therapy according to the present invention.

Figure 10:
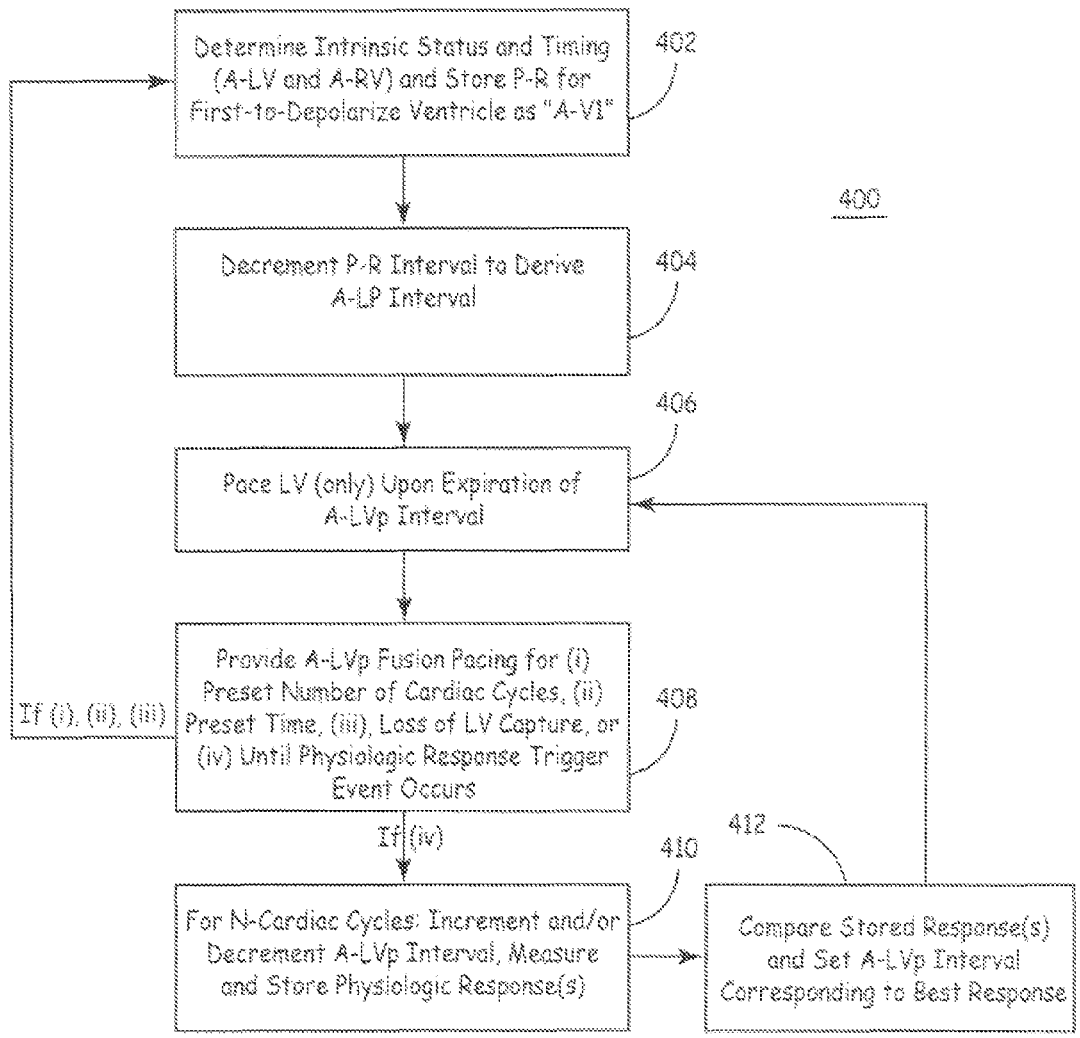
FIGS. 10-12 are flow charts depicting a few embodiments and/or aspects of the present invention.
Figure 11:
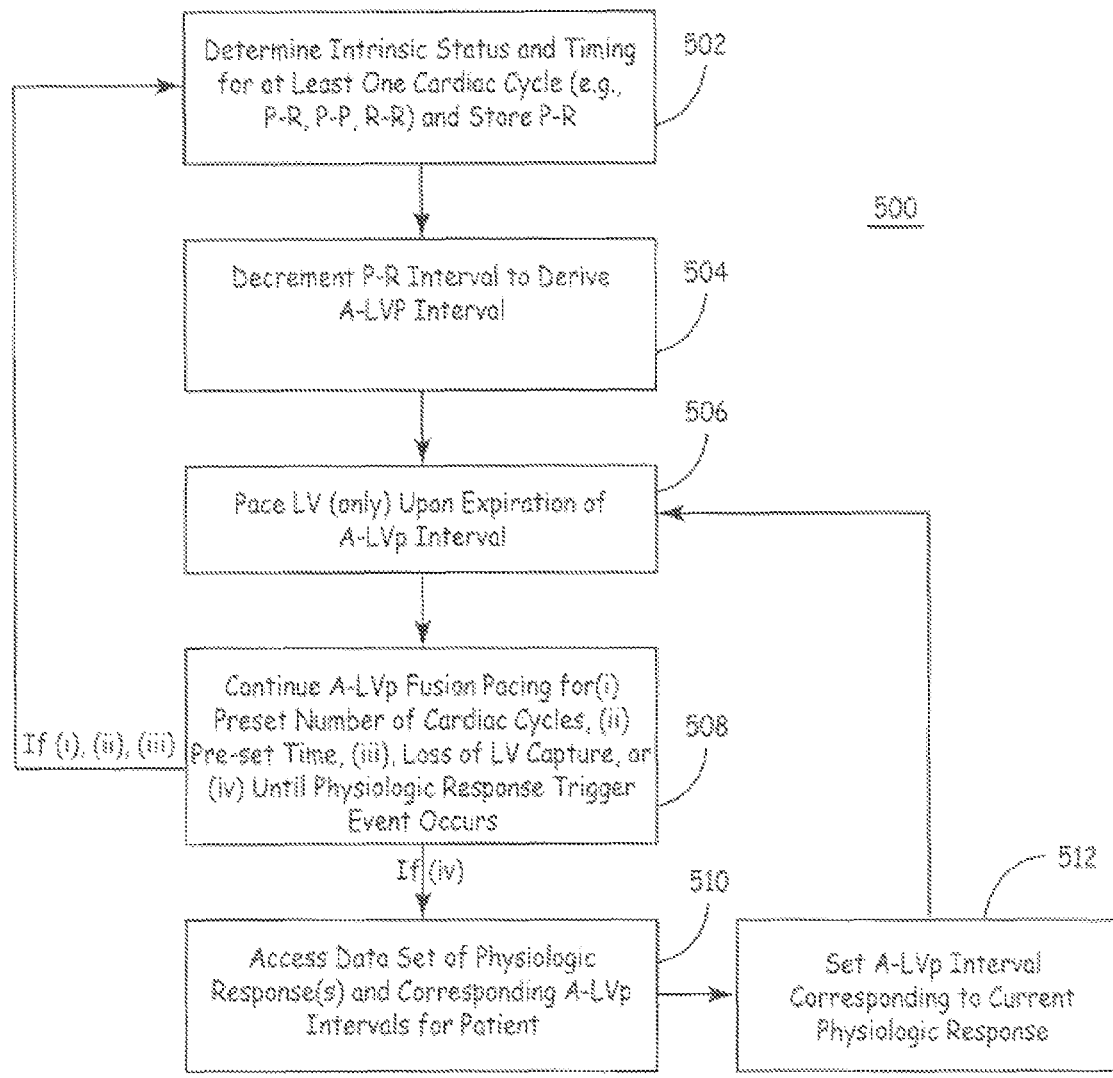
Figure 12:
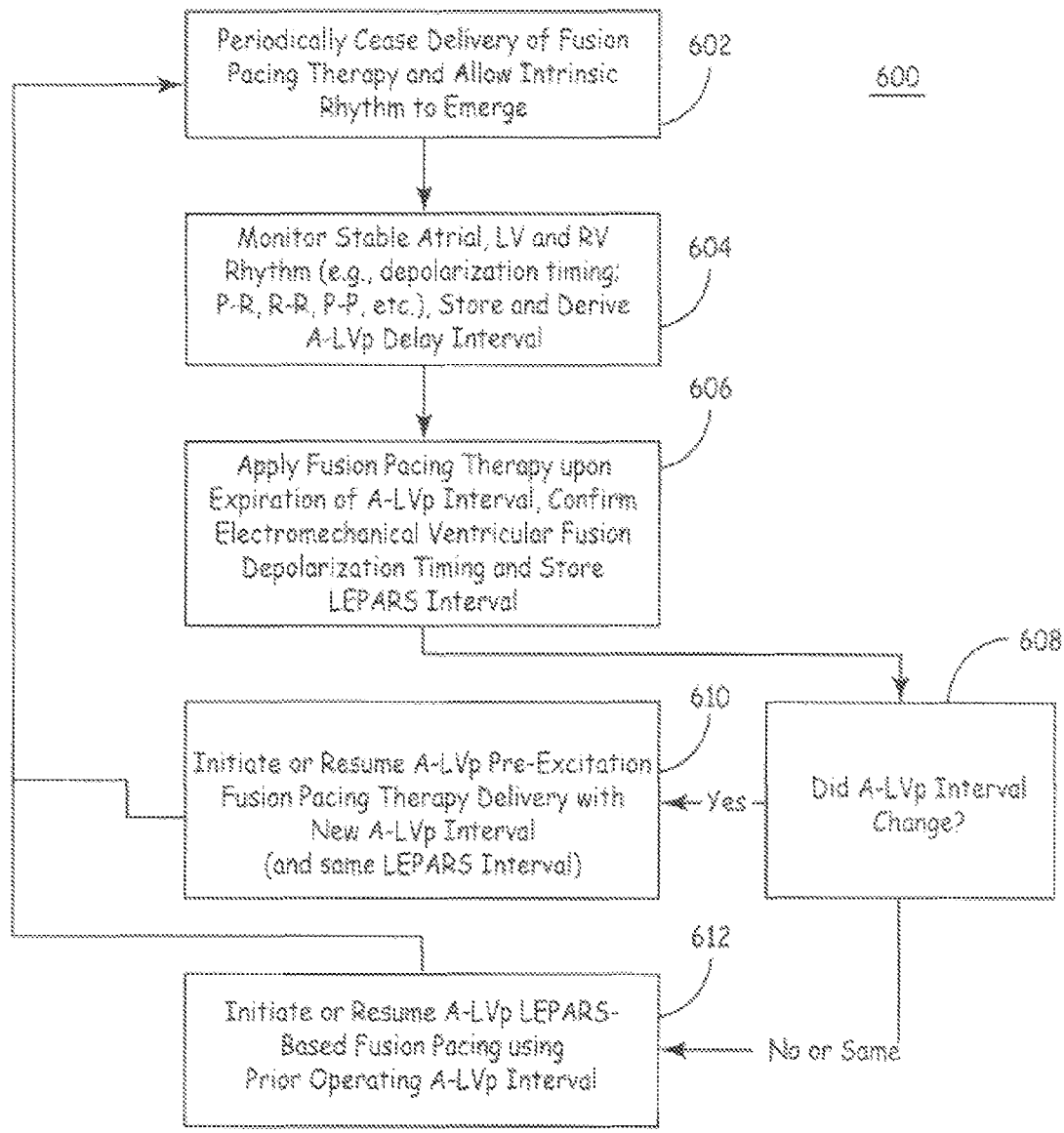

Some of the operating modes of IPG circuit 300 according to the present invention are depicted in the flow charts (FIGS. 10-12) and described as follows. The particular operating mode of the present invention is a programmed or hard-wired sub-set of the possible operating modes as also described below. For convenience, the algorithm of FIGS. 10-12 is described in the context of determining the A-LVp delay intervals to optimally pace the LV chamber to produce electromechanical fusion with the corresponding depolarization of the RV chamber. The RV chamber depolarizes intrinsically so that the pre-excited electromechanical fusion occurs as between the intrinsically activated RV chamber and the evoked response of the LV chamber. As noted below, the algorithm can be employed to determine an optimal A-LVp delay that results in ventricular synchrony (i.e., CRT delivery via a single ventricular pacing stimulus). Of course, the methods according to the present invention are intended to be stored as executable instructions on any appropriate computer readable medium although they may be performed manually as well.

FIG. 10 illustrates one embodiment of the present invention wherein the IPG circuit 300 includes a method 400 beginning with step 402 that is periodically performed to determine the intrinsic ventricular delay between the LV and the RV. In step 402, which can be performed on one or more consecutive cardiac cycles, the physiologic P-R interval is measured and stored (for the RV only for patients suffering from LBBB). In step 404 the physiologic P-R interval is decremented to generate a pre-excitation pacing interval for the LV chamber ("A-LVp"). The magnitude that the P-R interval is decremented depends on several factors. Some representative factors that can influence the decrement of the A-LVp delay include internal circuitry processing delay, location of sensing electrodes, heart rate, dynamic physiologic conduction status (e.g., due to ischemia, myocardial infarction, conduction fiber or bundle branch defects, etc.). However, the inventors have found that a decrement of approximately 20-40 milliseconds (ms) oftentimes provides approximately the longest operating A-V interval that maximizes a ventricular fusion response and adequate pre-excitation to the LV chamber resulting in electromechanical fusion of both ventricles. Nominally, a decrement of about 30 ms from the P-R interval has provided the advantages of the present invention. Of course, an iterative subroutine for decrementing the A-LVp delay can be used and/or a clinical procedure utilized to help narrow a range of prospective values for the magnitude of the decrease in the A-LVp delay. According to this part of the present invention a series of decrements are implemented over a series of at least several cardiac cycles (as needed for the hemodynamic or contractile response to stabilize). The hemodynamic response can be gauged with external or internal sensors (e.g., surface ECG, intracardiac EGM, internal or endocardial pressure sensor, epicardial accelerometer, arterial flow sensor, etc.). Doppler echocardiography or ultrasound techniques may also be used to confirm the appropriate decrement of the A-LVp delay.

In another aspect, a data set is generated for a range of heart rates that correspond to measured A-LVp delay intervals. The data may include paced or intrinsic heart rate data (ppm and bpm, respectively). In this aspect of the invention, the data set can be employed as a guiding or a controlling factor during heart rate excursions for continuous delivery of the single ventricular pre-excitation pacing of the present invention. In one form of this aspect of the invention, internal physiologic sensor data may be used to guiding factor when determining an appropriate setting for the operating A-LVp interval.

In yet another aspect, a first data set of appropriate values of the A-LVp delay interval are based on evoked response (i.e., wherein the A-EVENT is a pacing event) and a second data set of appropriate values of the A-LVp delay interval are based on intrinsic response (i.e., wherein the A-EVENT is a natural atrial depolarization).

Following the decrementing step 404 the A-LVp delay interval is set and in step 406 LEPARS-based, pre-excitation pacing therapy is delivered. In addition, in step 406 (for at least one hemodynamically stable cardiac cycle), the timing of LV pacing and RV sensing events are also optionally measured and stored (as the LEPARS interval). During measurement and storage of the LEPARS interval one or more confirmatory tests should be performed (and/or cardiac data stored) to ensure that ventricular fusion resulted from the single ventricle pacing therapy. Such tests can include temporal ECG or EGM tracings of at least the resulting QRS complexes, acutely invasive or chronic LV or RV fluid pressure measurements, monitor signals from an accelerometer coupled to the myocardium, and the like.

During delivery of LV pacing according to the invention, the operating AV delay intervals are used to control, or maintain, the LEPARS interval. That is, the LEPARS interval should not be allowed to change substantially from its original value programmed during ventricular fusion pacing. This aspect of the invention results from the fact that the value of IVCT does not change appreciably, even during heart rate excursions from normal sinus rhythm (e.g., sinus tachycardia). The LEPARS interval is thus controlled in a simple feedback control loop wherein the LEPARS interval are linked to A-LVp delay interval measurements. The control mechanism can include data sets stored in computer readable memory (e.g., LUT) and/or can include a dynamically-responsive control loop based on current or recently cardiac activity. As a result, the LEPARS integral can remain relatively constant along with the amount of ventricular fusion resulting from the pacing therapy, over a wide variety of conditions.

In the presently illustrated embodiment of the invention, pre-excitation pacing therapy delivery continues until: a preset number of cardiac cycles occur, a pre-set time period expires, a loss of capture occurs in the LV chamber, or a physiologic response trigger event occurs. The physiologic response trigger will be described below. With respect to the other three situations, the number of cardiac cycles or the time period may be set to any clinically appropriate value, given the patient's physiologic condition (among other factors) before returning to step 402 and (re-)determining the physiologic P-R interval and deriving an operating A-LVp. If a loss of capture in the LV chamber is detected it could indicate that the LV pacing stimulus is being delivered too late (e.g., during the refractory period of the LV chamber) or that the LV pacing electrodes have malfunctioned or become dislodged. While the process 400 depicted in FIG. 10 reflect that under all the foregoing situations steps 402-406 should be performed following events (i)-(iii), the fusion pacing therapy could of course be discontinued or a mode switch could be performed to another pacing modality (e.g., an AAI, ADI, AAI/R, ADI/R, double chamber DDD or DDD/R, and the like).

With respect to the physiologic response trigger event(s)—as well as optionally with respect to condition (iii) wherein loss of capture of the LV chamber occurs due to inappropriate timing of the LV pacing stimulus—at step 410 an iterative closed-loop process for determining an appropriate A-LVp interval is performed. In step 410, the A-LVp interval is directly manipulated from a prior operating value while one or more physiologic response is monitored and/or measured and stored. As mentioned above with respect to step 404 with regard to decrementing the intrinsic A-RV interval to generate the operating A-LVp interval, a number of sensors may be employed. After storing the physiologic response data (and corresponding AV delay used during data collection) at step 412 the data is compared and the AV delay corresponding to the most favorable physiologic response is then programmed as the operating AV delay. The process then proceeds back to step 406 and the LV chamber receives pre-excitation pacing therapy upon the expiration of the physiologically-derived AV delay. Of course, of the foregoing steps, steps 402, 404, 406 may be performed substantially continuously wherein step 402 (deriving the AV from the intrinsic A-RV interval) is only performed occasionally (e.g., every ten cardiac cycles, during heart rate excursions, etc.). In this form of the invention, the magnitude of the decrement of the A-RV can be based upon one or more prior operating values (and several prior operating values, with the most recent receiving additional statistical weight). In addition to or in lieu of the foregoing a look up table (LUT) or other data compilation, as described above, may be utilized to guide or control the derivation of the AV value (as described in more detail with respect to FIG. 11).

Now turning to FIG. 11, another embodiment of a method according to the present invention is depicted as process 500. To begin process 500, the steps 502,504,506,508 correspond closely to the corresponding steps of process 400 (FIG. 10) just described. However, at step 510—in the event that condition (iv) of step 508 is declared—a data set (or LUT) of physiologic responses and corresponding AV (A-LVp) values for a given patient is accessed. At step 512 the A-LVp delay is programmed to a value corresponding to the current physiologic response trigger for the patient. Then, at step 506, fusion pacing ensues upon expiration of the newly programmed AV delay interval. A representative physiologic response trigger includes an upward or downward heart rate excursion, a sensed lack of ventricular synchrony (based on accelerometer, pressure, EGM or other physiologic data signals) and the like.

In FIG. 12, a process 600 for periodically ceasing delivery of the pre-excitation, single ventricular pacing therapy to perform a pacing mode switch to a different form of pre-excitation therapy, ceasing pre-excitation therapy, or allowing normal sinus rhythm to continue (chronically) is illustrated. The process 600 can be implemented as a part of steps 402,502 (or process 400 and 500, respectively) for determining the intrinsic A-RV interval or can be performed independently. In either case, process 600 is designed to help reveal improvement (or decline) of a patient's condition. In the former case, if so-called "reverse remodeling" of the myocardium occurs resulting in return of ventricular synchrony and improved hemodynamics and autonomic tone, pre-excitation therapy delivery may be temporarily or permanently terminated. The patient may, in the best scenario, be relieved of pacing therapy delivery altogether (programming the pacing circuitry to an ODO monitoring-only "pacing modality"). Assuming the patient is not chronotropically incompetent, normal sinus rhythm may emerge permanently for all the activities of daily living. Additionally, the process 600 may be employed to search for a change in conduction status (e.g., wherein A-V conduction timing changes, etc.). According to process 600, at step 602 the delivery of LV-only fusion pacing therapy ceases and for at least one cardiac cycle the intrinsic, normal sinus rhythm is allowed to emerge. At step 604 during stable normal sinus rhythm depolarization(s) of the atria, LV and RV are monitored and, optionally stored in memory (e.g., P-P, P-R, R-R, etc.) and the A-LVp interval derived. At step 606 LEPARS-based fusion pacing is applied and when fusion is declared the operative LEPARS interval is stored. At step 608, the process 600 checks to determine if the AV interval has been modified (e.g., due to rate response, programming changes, normal sinus rhythm—in a tracking mode, etc.). In the event that the A-LVp interval has changed from a prior operating value, the method proceeds to step 610 wherein LV-only fusion pacing is initiated (or resumed) with a revised A-LVp interval, but substantially the same LEPARS interval. If the A-LVp interval has not changed appreciably from a prior operating value then the A-LVp LEPARS-based fusion pacing of the present invention is resumed or initiated using the prior operating A-LVp interval and substantially the same LEPARS interval. With respect to the magnitude of change to the A-LVp interval required to trigger step 610, as mentioned above a threshold value (or range of values) may be used to trigger step 610 depending on whether the patient is deemed a "fusion responder" or not. In contrast, a so-called nonresponder patient (or relatively less-responding patient) can receive LV-only fusion pacing therapy over a relatively small range of A-V interval excursions before expeditiously mode-switching to a different pacing therapy or ceasing delivery of pacing therapy.

Figure 13:
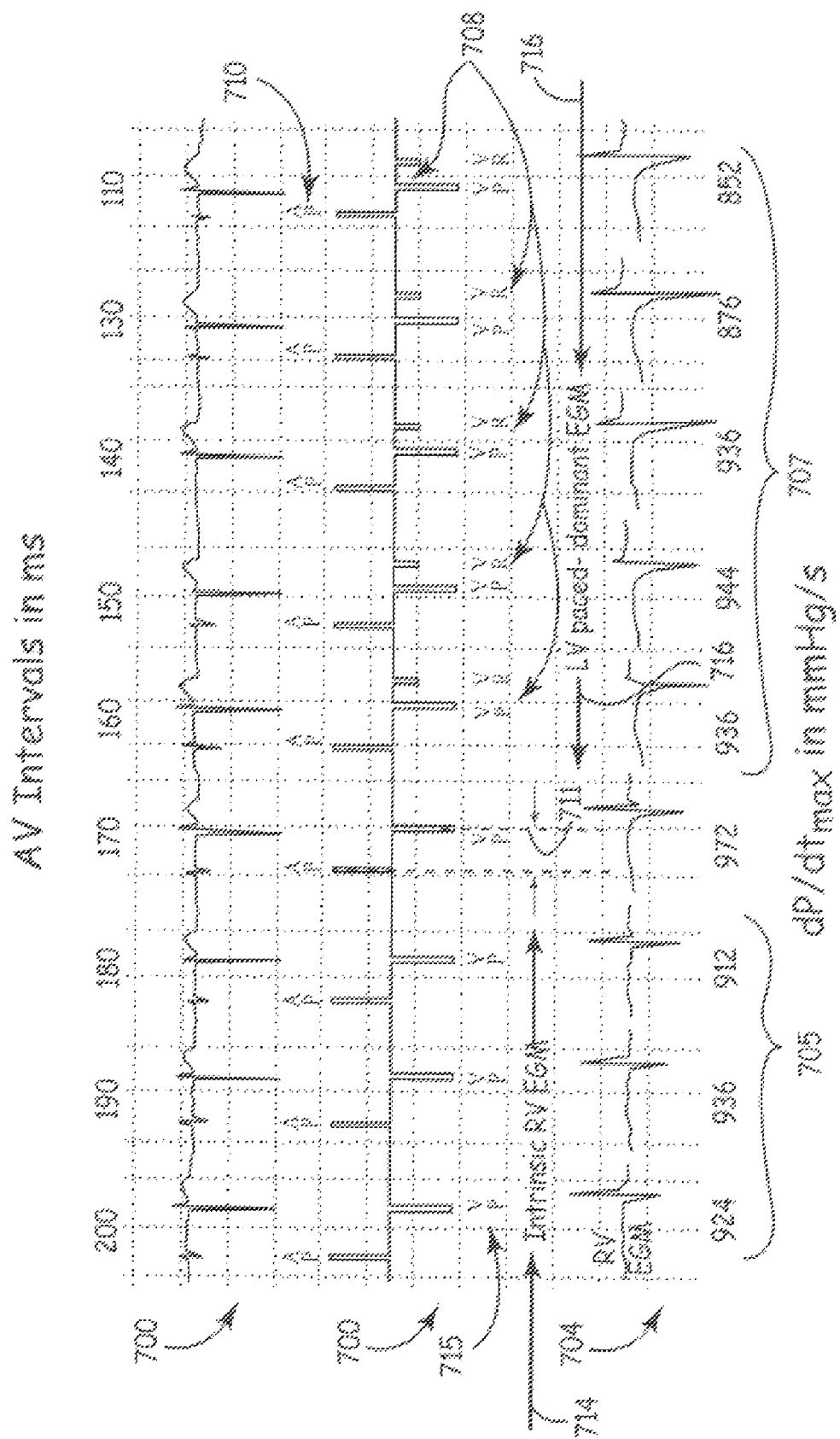
FIG. 13 is a temporal tracing of a surface ECG, a pacing "marker channel" composed of atrial pacing events (AP), LV pacing events (VP), and RV sensing events (VR)—because such events are deemed non-physiologic "refractory" events occurring too soon after the VP events, and resulting LV pressure development (dP/dt$_{max}$).

FIG. 13 is a temporal tracing of a surface ECG (denoted by arrow 700), a pacing "marker channel" composed of atrial pacing events (AP), LV pacing events (VP), and select RV sensing events (VR)—because such events are deemed non-physiologic "refractory" events occurring too soon after the VP events—(denoted by arrow 702), RV EGM (denoted by arrow 704), and resulting LV pressure development expressed as $dP/dt_{max}$ (denoted by arrows 705,706,707). The left-hand set of information corresponds to an A-LVp interval of 200 ms with 10 ms decrements for each other set of information (until the right-hand set of information corresponds to 110 ms A-LVp interval). At the relatively shorter AV intervals (denoted by parentheses 707) the LV pacing stimulus is denoted by "VP" and the RV sensed events are denoted as "VR" (708), or ventricular events incorrectly deemed non-physiologic due to the temporal proximity to the VP events. In FIG. 13 (at 707), developed pressure increases as the AV intervals are lengthened from 110 ms to 160 ms although no fusion depolarization have occurred. In contrast, at event 706 with the A-LVp interval set to 170 ms the "marker channel" (at 702) indicates a single VP event (and not independently-sensed "VR" event) and developed pressure reached a relative maximum value (972 mmHg/s). In addition, the morphology of the RV EGM 704 corresponding to the 170 ms AV interval confirms the presence of fusion depolarization(s). Thus, according to the invention, a LEPARS interval 711 promoting fusion resulting from LV-only pacing is defined as the time elapsed from Atrial activation (AP) to sensed RV depolarization (in FIG. 7 concealed as the "VP" event).

Thus, FIG. 13 illustrates a feature of the present invention; namely, the optimization of AV intervals based on EGM morphology changes. The premise is that the EGM reflects the source from which the wavefront is propagating from, the intrinsic RV conduction system, the LV pace, or a combination of the two. Identification of the transition point from intrinsic RV dominant to LV paced dominant coincides with a decrease in LV $dP/dt_{max}$ for LV only pacing. The AV interval should therefore be maintained above this level. This information can be coupled with the intrinsic A-RVs interval to define an optimal AV interval or range of optimal AV intervals.

The invention includes methods for using RV EGM morphology to automatically optimize the AV interval in several different ways. For example, and by way of illustration and without limitation:
 a) Manually via a programmer interface;
 b) Automatically on every beat or every n-beats;
 c) Automatically every x minutes or hours; and
 d) Automatically when a change in physiologic condition is detected (e.g. exercise).

The present invention provides methods for an automatic determination of the optimal AV interval or a range where the AV interval is near optimal. Presently, AV intervals are typically optimized through trans-thoracic echo evaluation or acute hemodynamic evaluations. These methods are not automatic and cannot be used within an implantable medical device.

In the past others have discussed the use of simple EGM morphology parameters for optimization of AV intervals in the context of CRT, but none have looked at more advanced signal processing techniques of EGM analysis to identify a transition from LV pacing dominated to RV sensing dominated EGM morphologies. The invention provides comparison of two or more EGM signal morphologies or other signals reflecting cardiac activity via one or more of the following:
 a) Peak-to-peak amplitude measurements;
 b) QT interval measurements;
 c) Timing of positive peak or peak derivative of the EGM;
 d) Timing of negative peak or minimum derivative of the EGM;
 e) Determination of the EGM as negative/positive or positive/negative;
 f) QRS or QRST area;
 g) Wavelet coefficients; and
 h) FFT coefficients.

In one of its simplest forms, the present invention is implemented using a programmer that provides temporal RV EGM output signals. According to the invention, an RV EGM is recorded during intrinsic conduction (no pacing) to give an RV sense-dominated EGM. The RV EGM will then be recorded during Atrial synchronous LV-only pacing at a relatively short AV interval (~30 ms or the shortest available AV delay) to provide an LV pace-dominated EGM. The AV interval is then progressively extended and the EGM morphologies recorded until an EGM morphology transition is identified from LV pace-dominated (denoted on FIG. 13 with arrows 716 and the phrase "LV pace dominant EGM") to RV sense-dominated (denoted on FIG. 13 with arrows 714 and the phrase "Intrinsic RV EGM") or until a maximum allowable AV interval is reached. The EGMs can be displayed in sequence for the clinician to interpret the point at which the EGM morphologies transition, allowing the clinician to determine the optimal AV interval. In lieu of manual inspection of the EGM traces, the invention provides for automatic analysis of the EGM morphologies to determine the transition point. In one form of the invention a combination of manual and automatic analysis is utilized that offers increased confidence in the conclusion. The automated analysis can be performed by analyzing changes in:
 a) Peak-to-peak amplitude measurements;
 b) QT interval measurements;
 c) Timing of positive peak or peak derivative of the EGM;
 d) Timing of negative peak or minimum derivative of the EGM;
 e) Determination of the EGM as negative/positive or positive/negative;
 f) QRS or QRST area;
 g) Wavelet coefficients of the EGM; and
 h) FFT coefficients of the EGM.

In lieu of or in addition to the foregoing, a fusion/transition point can also be determined based on the presence or absence of an RV refractory ventricular sense (VR), which the inventors have observed disappears with the RV sense-dominated EGM morphology.

The invention can be further enhanced through implementation of an algorithm within the device to automatically run the above algorithm to first determine the minimum AV interval using the transition point; second, determine or monitor the intrinsic A-RVs interval (maximum AV), and third, use an algorithm such as LEPARS to maintain the A-LV pace interval within an optimal bandwidth of the AV interval. This could be manually initiated by the physician, periodically by the device (e.g., on the order of minutes, hours, or days), or when a change in physiologic state is determined (e.g. increased activity or worsening heart failure). A different mode of the invention can be implemented on a beat-to-beat or every n-beat basis. Once an optimal AV interval (or range) is determined, the algorithm will then monitor the EGM morphology and adjust the AV interval to maintain the same morphology or, for example, to maintain the AV interval on the intrinsic RV dominant side of the transition point. If a shift towards an LV pace-dominant morphology occurs, the AV is lengthened. If a shift towards an RV sense-dominated morphology occurs, the AV is shortened.

In yet another implementation, when the LVpace-RVsense interval (IVCT) can be reliably measured, the bandwidth of the optimal AV interval is determined by the interval between the intrinsic A-RVs interval (RV sense-dominated morphology of the EGM) and the AV interval resulting in the first transition of the RV EGM. The optimal bandwidth should set the limits for the changes in AV interval but the optimal AV interval can be determined by the Lvpace-RVsense interval.

The EGM source can be based on a bipolar or unipolar EGM recorded anywhere within the heart, a coil-type EGM, a can-based EGM, surface ECG vector, or pseudo ECG and the like. One or more EGM or ECG sources could be analyzed for morphology changes for redundancy and to increase confidence in the conclusion.

The optimal AV interval may vary with lead placement and patient etiology. Therefore the optimal may not be exactly at the point of transition. Thus, the optimal AV can be set with respect to the EGM transition (+ or −5 to 40 ms).

A summary/restatement of the a clinical effort to study the issues addressed by the present invention includes, without limitation, the following: In patients with normal atrioventricular (AV) conduction LV pacing is superior to biventricular (BiV) pacing, due to intrinsic conduction over the right bundle branch during LV pacing. To investigate the hemodynamic effect of LV pacing and its association with the right ventricular (RV) electrogram (EGM) as an indicator of ventricular fusion. A BiV pacing system was implanted in 13 patients (8 males, age 66.8±10.2 years) with heart failure New York Heart Association (NYHA) class III-IV, ejection fraction 21.1±5.6% and sinus rhythm with normal AV conduction. The hemodynamic effect of LV, BiV simultaneous and (BiVsim) optimized V-V interval (BiV opt) pacing was evaluated by invasive measurement of LV rate-of-change ($dP/dt_{max}$) with different AV intervals. A 12 lead ECG and the RV EGM obtained via pacemaker telemetry were recorded and used to evaluate under what circumstances and with which timing intervals fusion depolarizations were obtained. The RV EGM showed a dominant R wave with AV intervals starting 30 ms below the intrinsic PR time (RV R-wave), changing to a configuration with a dominant S wave at short AV delays where no fusion was present (RV S-wave). In between an intermediate RV EGM morphology is recorded (RV-inter). LV dP/dtmax for baseline was 756±167, LV (RV R-wave) 936±209, LV (RV inter) 856±193, LV (RV S-wave) 787±176, BiV (simultaneous activation) 896±217 and BiVopt 936±216 mmHg/s. Thus, the inventors have discovered that LV-only fusion pacing with the optimal AV interval (LV opt) is hemodynamically superior to BiV (p=0.04) and approximately equal to BiVopt pacing. A change in the RV EGM from a prominent R wave to an intermediate morphology during LV pacing is associated with a significant decrease in LV dP/dtmax (p=0.0022). The change in the RV EGM indicates a shift in the extent of fusion from LV pacing.

Of course, certain of the above-described structures, functions and operations of the pacing systems of the illustrated embodiments are not necessary to practice the present invention and are included in the description simply for completeness of an exemplary embodiment or embodiments. It will also be understood that there may be other structures, functions and operations ancillary to the typical operation of an implantable pulse generator that are not disclosed and are not necessary to the practice of the present invention. It is therefore to be understood, that within the scope of the appended claims, the invention may be practiced otherwise than as specifically described without actually departing from the spirit and scope of the present invention and specifically set forth in the appended claims.

The invention claimed is:

1. A method of optimizing atrio-ventricular (AV) intervals for an single-ventricular fusion pacing therapy delivery, comprising:
   obtaining a sense-dominated signal indicative of intrinsic ventricular activity;
   obtaining a pacing-dominated signal indicative of paced ventricular activity, wherein the pacing-dominated signal is obtained during pacing therapy delivery utilizing a relatively short AV interval;
   progressively extending the relatively short AV interval and recording one of a set of fusion/transition-candidate signals for each newly extended AV interval;
   identifying a fusion/transition signal from the set of fusion/transition-candidate signals; and
   programming the newly extended AV interval that produced the fusion/transition signal as an operating AV interval; and
   wherein the paced ventricular activity comprises atrial synchronous left ventricular only (LVO) pacing therapy delivery.

2. A method according to claim 1, further comprising:
   correlating one of the relatively short AV interval and the newly extended AV intervals to its corresponding fusion/transition-candidate signals or fusion/transition signal.

3. A method according to claim 1, wherein the relatively short AV interval comprises an interval of about 30 milliseconds (ms) and or a shortest programmable AV interval for a given pulse generator.

4. A method according to claim 1, wherein both the sense-dominated signal and the pace-dominated signal are collected from a ventricular location.

5. A method according to claim 4, wherein the ventricular location comprises a right ventricular location.

6. A method according to claim 5, wherein the right ventricular location comprises one of an endocardial location and an epicardial location.

7. A method according to claim 1, wherein the sense-dominated signal and the pacing-dominated signal are derived from a right ventricular electrogram (RV EGM).

8. An apparatus for optimizing atrio-ventricular (AV) intervals for an single-ventricular fusion pacing therapy delivery, comprising:
   means for obtaining a sense-dominated signal indicative of intrinsic ventricular activity;
   means for obtaining a pacing-dominated signal indicative of paced ventricular activity, wherein the pacing-dominated signal is obtained during pacing therapy delivery utilizing a relatively short AV interval;
   means for progressively extending the relatively short AV interval and recording one of a set of fusion/transition-candidate signals for each newly extended AV interval;
   means for identifying a fusion/transition signal from the set of fusion/transition-candidate signals; and
   means for programming the newly extended AV interval that produced the fusion/transition signal as an operating AV interval.
   wherein the means for obtaining a pacing-dominated signal comprises means for delivering atrial synchronous left ventricular only (LVO) pacing therapy.

9. An apparatus according to claim 8, further comprising means for correlating one of the relatively short AV interval and the newly extended AV intervals to one of its corresponding fusion/transition-candidate signals and its fusion/transition signal.

10. A non-transitory computer readable medium for optimizing atrio- ventricular (AV) intervals for an single-ventricular fusion pacing therapy delivery, comprising:
   instructions for obtaining a sense-dominated signal indicative of intrinsic ventricular activity;
   instructions for obtaining a pacing-dominated signal indicative of paced ventricular activity, wherein the pacing-dominated signal is obtained during pacing therapy delivery utilizing a relatively short AV interval;
   instructions for extending the relatively short AV interval and recording one of a set of fusion/transition-candidate signals for each newly extended AV interval; instructions for identifying a fusion/transition signal from the set of fusion/transition-candidate signals;
   instructions for programming the newly extended AV interval that produced the fusion/transition signal as an operating AV interval; and
   wherein the instructions for obtaining a pacing-dominated signal comprise instructions for delivering atrial synchronous left ventricular only (LVO) pacing therapy.

11. A medium according to claim 10, further comprising instructions for correlating one of the relatively short AV interval and the newly extended AV intervals to one of its corresponding fusion/transition-candidate signals and its fusion/transition signal.

12. A non-transitory computer readable medium for optimizing atrio- ventricular (AV) intervals for an single-ventricular fusion pacing therapy delivery, comprising:
   Instructions for obtaining a sense-dominated signal indicative of intrinsic ventricular activity;
   instructions for obtaining a pacing-dominated signal indicative of paced ventricular activity, wherein the pacing-dominated signal is obtained during pacing therapy delivery utilizing a relatively short AV interval;
   instructions for extending the relatively short AV interval and recording one of a set of fusion/transition-candidate signals for each newly extended AV interval instructions for identifying a fusion/transition signal from the set of fusion/transition-candidate signals;
   instructions for programming an operating AV interval that corresponds to the newly extended AV interval that produced the fusion/transition signal;
   wherein the instructions for obtaining a sense-dominated signal indicative of intrinsic ventricular activity comprise instructions for storing a temporal electrogram of the obtained signal; and
   wherein the instructions for obtaining a pacing-dominated signal comprise instructions for delivering atrial synchronous left ventricular only (LVO) pacing therapy.

13. A non-transitory computer readable medium for optimizing atrio-ventricular (AV) intervals for an single-ventricular fusion pacing therapy delivery, comprising:
   instructions for obtaining a sense-dominated signal indicative of intrinsic ventricular activity;
   instructions for obtaining a pacing-dominated signal indicative of paced ventricular activity, wherein the pacing-dominated signal is obtained during pacing therapy delivery utilizing a relatively short AV interval;
   instructions for extending the relatively short AV interval and recording one of a set of fusion/transition-candidate signals for each newly extended AV interval;
   instructions for identifying a fusion/transition signal from the set of fusion/transition-candidate signals;
   instructions for programming an operating AV interval that corresponds to the newly extended AV interval that produced the fusion/transition signal;
   wherein the instructions for obtaining a pacing-dominated signal indicative of intrinsic ventricular activity comprises storing a temporal electrogram of the obtained signal; and
   wherein the instructions for obtaining a pacing-dominated signal comprise instructions for delivering atrial synchronous left ventricular only (LVO) pacing therapy.

14. A non-transitory computer readable medium for optimizing atrio-ventricular (AV) intervals for an single-ventricular fusion pacing therapy delivery, comprising:
   instructions for obtaining a sense-dominated signal indicative of intrinsic ventricular activity;
   instructions for obtaining a pacing-dominated signal indicative of paced ventricular activity, wherein the pacing-dominated signal is obtained during pacing therapy delivery utilizing a relatively short AV interval;
   instructions for extending the relatively short AV interval and recording one of a set of fusion/transition-candidate signals for each newly extended AV interval; instructions for identifying a fusion/transition signal from the set of fusion/transition-candidate signals;
   instructions for programming an operating AV interval that corresponds to the newly extended AV interval that produced the fusion/transition signal;
   wherein the instructions for recording a fusion/transition-candidate signal comprise instructions for obtaining the fusion/transition-candidate signal and storing a temporal electrogram of the obtained signal; and
   wherein the instructions for obtaining a pacing-dominated signal comprise instructions for delivering atrial synchronous left ventricular only (LVO) pacing therapy.

15. A non-transitory computer readable medium according to claim 12 or claim 13 or claim 14 wherein the instructions for storing the obtained signal comprise instructions for obtaining at least one of the following characteristics:
   a peak-to-peak amplitude characteristic; a QT interval characteristic;
   a temporal location of a positive peak of the signal; a temporal location of a peak derivative of the signal;
   a temporal location of a negative peak of the signal; a temporal location of a minimum derivative of the signal;
   at least a portion of a QRS depolarization signal;
   at least a part of a depolarization-re-polarization QRS-T signal an integral of at least a portion of a QRS depolarization signal;
   an integral of at least a part of a depolarization-re-polarization QRS-T signal; a wavelet coefficient; a fast Fourier transform coefficient.

16. An apparatus for optimizing atrio-ventricular (AV) intervals for an single-ventricular fusion pacing therapy delivery, comprising:
   means for obtaining a sense-dominated signal indicative of intrinsic ventricular activity;
   means for obtaining a pacing-dominated signal indicative of paced ventricular activity, wherein the pacing-dominated signal is obtained during pacing therapy delivery utilizing a relatively short AV interval;
   means for progressively extending the relatively short AV interval and recording one of a set of fusion/transition-candidate signals for each newly extended AV interval; means for identifying a fusion/transition signal from the set of fusion/transition-candidate signals;
   means for programming an operating AV interval that corresponds to the newly extended AV interval that produced the fusion/transition signal; means for correlating one of the relatively short AV interval and the newly extended AV intervals to one of its corresponding fusion/transition-candidate signals and its fusion/transition signal;

wherein the means for obtaining a sense-dominated signal indicative of intrinsic ventricular activity comprises means for storing a temporal electrogram of the obtained signal; and wherein the means for obtaining a pacing-dominated signal comprises means for delivering atrial synchronous left ventricular only (LVO) pacing therapy.

17. An apparatus for optimizing atrio-ventricular (AV) intervals for an single-ventricular fusion pacing therapy delivery, comprising:

means for obtaining a sense-dominated signal indicative of intrinsic ventricular activity;

means for obtaining a pacing-dominated signal indicative of paced ventricular activity, wherein the pacing-dominated signal is obtained during pacing therapy delivery utilizing a relatively short AV interval;

means for progressively extending the relatively short AV interval and recording one of a set of fusion/transition-candidate signals for each newly extended AV interval;

means for identifying a fusion/transition signal from the set of fusion/transition-candidate signals;

means for programming an operating AV interval that corresponds to the newly extended AV interval that produced the fusion/transition signal;

wherein the means for obtaining a pacing-dominated signal indicative of intrinsic ventricular activity comprises means for storing a temporal electrogram of the obtained signal; and wherein the means for obtaining a pacing-dominated signal comprises means for delivering atrial synchronous left ventricular only (LVO) pacing therapy.

18. An apparatus for optimizing atrio-ventricular (AV) intervals for an single-ventricular fusion pacing therapy delivery, comprising:

means for obtaining a sense-dominated signal indicative of intrinsic ventricular activity;

means for obtaining a pacing-dominated signal indicative of paced ventricular activity, wherein the pacing-dominated signal is obtained during pacing therapy delivery utilizing a relatively short AV interval;

means for progressively extending the relatively short AV interval and recording one of a set of fusion/transition-candidate signals for each newly extended AV interval;

means for identifying a fusion/transition signal from the set of fusion/transition-candidate signals;

means for programming an operating AV interval that corresponds to the newly extended AV interval that produced the fusion/transition signal;

wherein the means for recording a fusion/transition-candidate signal comprises means for obtaining the fusion/transition-candidate signal and for storing a temporal electrogram of the obtained signal; and wherein the means for obtaining a pacing-dominated signal comprises means for delivering atrial synchronous left ventricular only (LVO) pacing therapy.

19. An apparatus according to claim 16 or 17 or 18, wherein the means for storing the obtained signal comprises means for obtaining at least one of the following characteristics: a peak-to-peak amplitude characteristic; a QT interval characteristic; a temporal location of a positive peak of the signal; a temporal location of a peak derivative of the signal; a temporal location of a negative peak of the signal; a temporal location of a minimum derivative of the signal; at least a portion of a QRS depolarization signal; at least a part of a depolarization-re-polarization QRS-T signal; an integral of at least a portion of a QRS depolarization signal; an integral of at least a part of a depolarization-re-polarization QRS-T signal; a wavelet coefficient; a fast Fourier transform coefficient.

20. A method of optimizing atrio-ventricular (AV) intervals for an single-ventricular fusion pacing therapy delivery, comprising:

obtaining a sense-dominated signal indicative of intrinsic ventricular activity;

obtaining a pacing-dominated signal indicative of paced ventricular activity, wherein the pacing-dominated signal is obtained during pacing therapy delivery utilizing a relatively short AV interval;

progressively extending the relatively short AV interval and recording one of a set of fusion/transition-candidate signals for each newly extended AV interval;

identifying a fusion/transition signal from the set of fusion/transition-candidate signals;

programming an operating AV interval that corresponds to the newly extended AV interval that produced the fusion/transition signal;

wherein obtaining a sense-dominated signal indicative of intrinsic ventricular activity comprises storing a temporal electrogram of the obtained signal; and wherein the paced ventricular activity comprises atrial synchronous left ventricular only (LVO) pacing therapy delivery.

21. A method of optimizing atrio-ventricular (AV) intervals for an single-ventricular fusion pacing therapy delivery, comprising:

obtaining a sense-dominated signal indicative of intrinsic ventricular activity;

obtaining a pacing-dominated signal indicative of paced ventricular activity, wherein the pacing-dominated signal is obtained during pacing therapy delivery utilizing a relatively short AV interval;

progressively extending the relatively short AV interval and recording one of a set of fusion/transition-candidate signals for each newly extended AV interval; identifying a fusion/transition signal from the set of fusion/transition-candidate signals;

programming an operating AV interval that corresponds to the newly extended AV interval that produced the fusion/transition signal;

wherein obtaining a pacing-dominated signal indicative of intrinsic ventricular activity comprises storing a temporal electrogram of the obtained signal; and wherein the paced ventricular activity comprises atrial synchronous left ventricular only (LVO) pacing therapy delivery.

22. A method of optimizing atrio-ventricular (AV) intervals for an single-ventricular fusion pacing therapy delivery, comprising:

obtaining a sense-dominated signal indicative of intrinsic ventricular activity; obtaining a pacing-dominated signal indicative of paced ventricular activity, wherein the pacing-dominated signal is obtained during pacing therapy delivery utilizing a relatively short AV interval;

progressively extending the relatively short AV interval and recording one of a set of fusion/transition-candidate signals for each newly extended AV interval; identifying a fusion/transition signal from the set of fusion/transition-candidate signals;

programming an operating AV interval that corresponds to the newly extended AV interval that produced the fusion/transition signal;

wherein recording a fusion/transition-candidate signal comprises obtaining the fusion/transition-candidate signal and storing a temporal electrogram of the obtained signal; and wherein the paced ventricular activity comprises atrial synchronous left ventricular only (LVO) pacing therapy delivery.

23. A method according to claim 11 or claim 16 wherein storing the obtained signal comprises obtaining at least one of the following characteristics: a peak-to-peak amplitude characteristic; a QT interval characteristic; a temporal location of a positive peak of the signal; a temporal location of a peak derivative of the signal; a temporal location of a negative peak of the signal; a temporal location of a minimum derivative of the signal; at least a portion of a QRS depolarization signal; at least a part of a depolarization-re-polarization QRS-T signal; an integral of at least a portion of a QRS depolarization signal; an integral of at least a part of a depolarization-re-polarization QRS-T signal; a wavelet coefficient; a fast Fourier transform coefficient.

* * * * *